United States Patent
Jain et al.

(10) Patent No.: US 10,362,998 B2
(45) Date of Patent: Jul. 30, 2019

(54) SENSOR-BASED DETECTION OF CHANGES IN HEALTH AND VENTILATION THRESHOLD

(71) Applicant: Samsung Electronics Co., Ltd., Gyeonggi-Do (KR)

(72) Inventors: Jawahar Jain, Los Altos, CA (US); Cody Wortham, Mountain View, CA (US); James Young, Menlo Park, CA (US); Sajid Sadi, San Jose, CA (US); Pranav Mistry, Campbell, CA (US); Abhijit Z. Bendale, Sunnyvale, CA (US)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 0 days.

(21) Appl. No.: 15/436,054

(22) Filed: Feb. 17, 2017

(65) Prior Publication Data
US 2017/0245808 A1    Aug. 31, 2017

Related U.S. Application Data

(60) Provisional application No. 62/299,960, filed on Feb. 25, 2016, provisional application No. 62/300,020, (Continued)

(51) Int. Cl.
*A61B 5/00* (2006.01)
*A61B 5/11* (2006.01)
(Continued)

(52) U.S. Cl.
CPC .......... *A61B 5/7282* (2013.01); *A61B 5/0205* (2013.01); *A61B 5/02416* (2013.01); (Continued)

(58) Field of Classification Search
CPC combination set(s) only.
See application file for complete search history.

(56) References Cited

U.S. PATENT DOCUMENTS 5,144,949 A    9/1992    Olson
5,410,472 A    4/1995    Anderson
(Continued)

FOREIGN PATENT DOCUMENTS

EP    0559847 A1    9/1993
EP    1192971 A2    8/2001
(Continued)

OTHER PUBLICATIONS

Int'l. Appln. No. PCT/KR2017/002043, Int'l. Search Report, dated Apr. 28, 2017, 3 pg.
(Continued)

*Primary Examiner* — Niketa I Patel
*Assistant Examiner* — Shirley X Jian
(74) *Attorney, Agent, or Firm* — Cuenot, Forsythe & Kim, LLC

(57) ABSTRACT

Monitoring health status of a user may be performed by an apparatus that includes a sensor adapted to generate sensor data, a memory adapted to store a plurality of baseline biological markers for a user, wherein the plurality of baseline biological markers include respiratory rhythm, and a processor coupled to the memory and the sensor. The processor is adapted to, in response to detecting that the user is performing physical activity, determine a biological marker from the sensor data. The processor is adapted to compare the biological marker with the baseline biological marker. The processor is further adapted to, in response to detecting a change in the biological marker, provide a notification indicating a change in health status.

10 Claims, 6 Drawing Sheets

Related U.S. Application Data filed on Feb. 25, 2016, provisional application No. 62/300,024, filed on Feb. 25, 2016.

(51) Int. Cl.
  *A61B 5/0205* (2006.01)
  *A61B 5/08* (2006.01)
  *A61B 5/024* (2006.01)
  *A61B 5/1495* (2006.01)
  *G16H 50/30* (2018.01)
  *G16H 40/60* (2018.01)

(52) U.S. Cl.
  CPC .......... *A61B 5/0816* (2013.01); *A61B 5/1118* (2013.01); *A61B 5/1495* (2013.01); *A61B 5/7246* (2013.01); *A61B 5/7275* (2013.01); *A61B 5/746* (2013.01); *G16H 40/60* (2018.01); *G16H 50/30* (2018.01); *A61B 5/0015* (2013.01); *A61B 5/0059* (2013.01); *A61B 5/024* (2013.01); *A61B 5/7475* (2013.01)

(56) References Cited

U.S. PATENT DOCUMENTS

| | | | |
|---|---|---|---|
| 6,077,222 A | 6/2000 | Lloyd et al. | |
| 6,472,988 B1 | 10/2002 | Feld et al. | |
| 6,540,674 B2 | 4/2003 | Zadrozny et al. | |
| 6,904,311 B2 | 6/2005 | Freeberg | |
| 7,142,920 B2 | 11/2006 | Scheiner et al. | |
| 7,674,226 B2* | 3/2010 | Nadeau | A61B 5/14546 600/300 |
| 7,785,242 B2 | 8/2010 | Solomon | |
| 7,853,455 B2 | 12/2010 | Brown | |
| 7,869,877 B2 | 1/2011 | Kadhiresan | |
| 7,877,277 B1 | 1/2011 | Petit et al. | |
| 7,974,708 B2 | 7/2011 | Daum et al. | |
| 7,993,268 B2* | 8/2011 | Nadeau | A61B 5/14546 600/300 |
| 8,118,712 B2* | 2/2012 | Thieberger | A63B 24/0062 482/1 |
| 8,200,323 B2* | 6/2012 | DiBenedetto | A63B 24/0062 600/519 |
| 8,660,625 B2* | 2/2014 | Addison | A61B 5/14551 600/323 |
| 8,719,214 B2 | 5/2014 | Stergiou et al. | |
| 8,738,133 B2 | 5/2014 | Shuros et al. | |
| 8,768,489 B2* | 7/2014 | Thieberger | A63B 24/0062 607/122 |
| 8,781,564 B2 | 7/2014 | Kinnunen | |
| 8,876,688 B2 | 11/2014 | Hyde et al. | |
| 8,897,522 B2 | 11/2014 | Mestha et al. | |
| 8,903,491 B2 | 12/2014 | Hopper et al. | |
| 8,956,290 B2 | 2/2015 | Gilley et al. | |
| 8,986,206 B2 | 3/2015 | Kim et al. | |
| 9,002,427 B2 | 4/2015 | Tupin, Jr. et al. | |
| 9,020,185 B2 | 4/2015 | Mestha et al. | |
| 9,027,552 B2 | 5/2015 | Angelico et al. | |
| 9,028,258 B2 | 5/2015 | Burdea | |
| 9,035,778 B2 | 5/2015 | Howie et al. | |
| 9,070,267 B2 | 6/2015 | Hanson et al. | |
| 9,089,760 B2 | 7/2015 | Tropper et al. | |
| 9,106,307 B2 | 8/2015 | Molettiere et al. | |
| 9,128,305 B2 | 9/2015 | Honore et al. | |
| 9,132,275 B2 | 9/2015 | Yu et al. | |
| 9,135,347 B2 | 9/2015 | Damman et al. | |
| 9,161,698 B2 | 10/2015 | Zhang et al. | |
| 9,168,017 B2 | 10/2015 | Ward et al. | |
| 9,171,196 B2 | 10/2015 | Wang et al. | |
| 9,173,615 B2 | 11/2015 | Katra et al. | |
| 9,180,140 B2 | 11/2015 | Lundberg et al. | |
| 9,185,353 B2 | 11/2015 | Mestha et al. | |
| 9,204,836 B2 | 12/2015 | Bender et al. | |
| 9,220,440 B2 | 12/2015 | Addison et al. | |
| 9,232,894 B2 | 1/2016 | Tesanovic et al. | |
| 9,232,897 B2 | 1/2016 | Thakur et al. | |
| 9,232,910 B2 | 1/2016 | Alshaer et al. | |
| 9,247,884 B2 | 2/2016 | Yuen et al. | |
| 9,248,306 B2 | 2/2016 | Joo et al. | |
| 9,250,104 B2 | 2/2016 | Greiner et al. | |
| 9,262,772 B2 | 2/2016 | Stivoric et al. | |
| 9,265,477 B2 | 2/2016 | Yang et al. | |
| 9,268,908 B2 | 2/2016 | Ashdown et al. | |
| 9,286,789 B2 | 3/2016 | Park et al. | |
| 9,294,898 B2 | 3/2016 | Shikama et al. | |
| 9,665,873 B2* | 5/2017 | Ackland | A63B 24/0075 |
| 10,172,517 B2* | 1/2019 | Jain | A61B 5/0002 |
| 2004/0006492 A1 | 1/2004 | Watanabe | |
| 2005/0070809 A1 | 3/2005 | Acres | |
| 2006/0218007 A1 | 9/2006 | Bjorner et al. | |
| 2007/0024946 A1 | 2/2007 | Panasyuk et al. | |
| 2007/0179350 A1* | 8/2007 | Nadeau | A61B 5/14546 600/300 |
| 2007/0185391 A1 | 8/2007 | Morgan | |
| 2007/0207437 A1 | 9/2007 | Sachdeva et al. | |
| 2008/0150714 A1 | 6/2008 | Bauer et al. | |
| 2009/0058660 A1 | 3/2009 | Torch | |
| 2009/0076343 A1 | 3/2009 | James et al. | |
| 2009/0234406 A1* | 9/2009 | Shuros | A61N 1/36114 607/11 |
| 2009/0271347 A1 | 10/2009 | Hyde et al. | |
| 2009/0312151 A1* | 12/2009 | Thieberger | A63B 24/0062 482/8 |
| 2009/0312658 A1* | 12/2009 | Thieberger | A63B 24/0062 600/520 |
| 2010/0009328 A1* | 1/2010 | Nadeau | A61B 5/14546 434/247 |
| 2010/0249531 A1 | 9/2010 | Hanlon et al. | |
| 2010/0256512 A1 | 10/2010 | Sullivan | |
| 2010/0292599 A1* | 11/2010 | Oleson | A63B 24/0062 600/519 |
| 2010/0292600 A1* | 11/2010 | DiBenedetto | A63B 24/0062 600/520 |
| 2010/0298899 A1 | 11/2010 | Donnelly et al. | |
| 2011/0270049 A1 | 11/2011 | Katra et al. | |
| 2011/0295084 A1 | 12/2011 | Thakur et al. | |
| 2012/0010504 A1 | 1/2012 | Furlan | |
| 2012/0029936 A1 | 2/2012 | Hanoun | |
| 2012/0109243 A1 | 5/2012 | Hettrick et al. | |
| 2012/0145152 A1* | 6/2012 | Lain | A61M 16/0051 128/204.23 |
| 2012/0157856 A1 | 6/2012 | An et al. | |
| 2012/0253207 A1 | 10/2012 | Sarkar et al. | |
| 2012/0259649 A1 | 10/2012 | Mallon et al. | |
| 2013/0024212 A1 | 1/2013 | Atakhorrami et al. | |
| 2013/0079646 A1 | 3/2013 | Bhunia et al. | |
| 2013/0092165 A1* | 4/2013 | Wondka | A61M 15/08 128/204.25 |
| 2013/0197381 A1 | 8/2013 | Charlton et al. | |
| 2013/0209977 A1 | 8/2013 | Lathan et al. | |
| 2013/0261479 A1 | 10/2013 | Kemppainen et al. | |
| 2013/0281798 A1 | 10/2013 | Rau et al. | |
| 2014/0006041 A1 | 1/2014 | Steinhauer et al. | |
| 2014/0051047 A1 | 2/2014 | Bender et al. | |
| 2014/0051941 A1 | 2/2014 | Messerschmidt | |
| 2014/0052475 A1 | 2/2014 | Madan et al. | |
| 2014/0058745 A1 | 2/2014 | Ji et al. | |
| 2014/0061047 A1 | 3/2014 | Stich et al. | |
| 2014/0081432 A1 | 3/2014 | Kingon et al. | |
| 2014/0100822 A1 | 4/2014 | Hiltner | |
| 2014/0107500 A1 | 4/2014 | Stamatopoulos et al. | |
| 2014/0112559 A1 | 4/2014 | Freeman et al. | |
| 2014/0114147 A1 | 4/2014 | Romesburg | |
| 2014/0149465 A1 | 5/2014 | Kannan et al. | |
| 2014/0155773 A1 | 6/2014 | Stamatopoulos et al. | |
| 2014/0171776 A1 | 6/2014 | Lin et al. | |
| 2014/0172442 A1 | 6/2014 | Broderick et al. | |
| 2014/0228649 A1 | 8/2014 | Rayner et al. | |
| 2014/0243686 A1 | 8/2014 | Kimmel | |
| 2014/0267668 A1 | 9/2014 | Ignatovich et al. | |
| 2014/0276549 A1 | 9/2014 | Osorio | |
| 2014/0371604 A1* | 12/2014 | Katra | A61B 5/0002 600/484 |

(56) References Cited

U.S. PATENT DOCUMENTS

| | | | |
|---|---|---|---|
| 2015/0011361 A1 | 1/2015 | Boyette et al. | |
| 2015/0031965 A1 | 1/2015 | Visvanathan et al. | |
| 2015/0038854 A1 | 2/2015 | Zhang et al. | |
| 2015/0065825 A1 | 3/2015 | Utley et al. | |
| 2015/0065898 A1 | 3/2015 | Prstojevich et al. | |
| 2015/0099952 A1* | 4/2015 | Lain | A61B 5/0205 600/324 |
| 2015/0125832 A1 | 5/2015 | Tran | |
| 2015/0165271 A1 | 6/2015 | Sung-Lien et al. | |
| 2015/0202492 A1 | 7/2015 | Domansky et al. | |
| 2015/0213217 A1 | 7/2015 | Amarasingham et al. | |
| 2015/0269851 A1 | 9/2015 | Lee et al. | |
| 2015/0305675 A1 | 10/2015 | Miller et al. | |
| 2015/0305683 A1 | 10/2015 | Frix et al. | |
| 2015/0317438 A1 | 11/2015 | Ingrassia, Jr. et al. | |
| 2015/0352147 A1 | 12/2015 | Lundberg et al. | |
| 2015/0359845 A1 | 12/2015 | Marban et al. | |
| 2015/0370993 A1* | 12/2015 | Moturu | G06F 19/3418 703/6 |
| 2015/0370994 A1 | 12/2015 | Madan et al. | |
| 2015/0374289 A1 | 12/2015 | Teller et al. | |
| 2015/0379477 A1 | 12/2015 | Junqua et al. | |
| 2016/0008957 A1 | 1/2016 | Kaur et al. | |
| 2016/0022193 A1 | 1/2016 | Rau et al. | |
| 2016/0045168 A1 | 2/2016 | Storer et al. | |
| 2016/0058336 A1 | 3/2016 | Blahnik et al. | |
| 2016/0063205 A1 | 3/2016 | Moturu et al. | |
| 2016/0091922 A1 | 3/2016 | Nazzaro et al. | |
| 2016/0345841 A1* | 12/2016 | Jang | A61B 5/0205 |
| 2016/0354636 A1* | 12/2016 | Jang | A61B 5/02438 |
| 2017/0245759 A1* | 8/2017 | Jain | A61B 5/0002 |
| 2017/0245805 A1 | 8/2017 | Jain et al. | |
| 2017/0249437 A1 | 8/2017 | Jain et al. | |
| 2017/0249438 A1 | 8/2017 | Jain et al. | |
| 2017/0282011 A1* | 10/2017 | Jang | G09B 5/02 |
| 2017/0296104 A1* | 10/2017 | Ryan | A61B 5/1118 |

FOREIGN PATENT DOCUMENTS

| | | |
|---|---|---|
| EP | 1667578 | 9/2004 |
| EP | 2739207 A2 | 6/2014 |
| EP | 2897067 A1 | 7/2015 |
| KR | 20000006830 A | 2/2000 |
| KR | 100545772 B1 | 1/2006 |
| KR | 20060092557 A | 8/2006 |
| KR | 20130010207 A | 1/2013 |
| WO | 9216258 A1 | 10/1992 |
| WO | 01008755 A1 | 2/2001 |
| WO | 02018019 A1 | 3/2002 |
| WO | 2011032132 A2 | 3/2011 |
| WO | 2013036853 A2 | 3/2013 |
| WO | 20140147496 A1 | 9/2014 |
| WO | 2015178637 A1 | 11/2015 |
| WO | 2016049425 S1 | 3/2016 |

OTHER PUBLICATIONS

Int'l. Appln. No. PCT/KR2017/002043, Written Opinion, dated Apr. 28, 2017, 8 pg.

U.S. Appl. No. 15/436,920, Non-Final Office Action, dated Mar. 7, 2018, 11 pg.

Lee, J. et al., "Atrial Fibrillation Detection using a Smart Phone," In 34th Annual Int'l. Conf. of the IEEE Engineering in Medicine and Biology Society (EMBC), Sep. 1, 2012, pp. 1177-1180.

"Web Cam Used to Detect Abnormal Heart Rhythm," [online] Reuters Health, In the Journal of mHealth, Oct. 15, 2014., vol. 1, No. 5, pp. 16-17, retrieved from the Internet: <https://www.joomag.com/magazine/the-journal-of-mhealth-vol-1-issue-5-oct-2014/0194692001413453930?page=18>.

Melzer, C. et al, Predictors of Chronotropic Incompetence in the Pacemaker Patient Population, In Europace, vol. 8, No. 1, Jan. 2006. pp. 70-75.

Melzer, C. et al., "Chronotropic Incompetence: a Never-Ending Story," In Europace, vol. 12, No. 4, Apr. 2010, pp. 464-465.

Lauer, M.S., "Heart Rate Response in Stress Testing: Clinical Implications," In ACC Current Journal Review, vol. 10, No. 5, pp. 16-19, Oct. 31, 2001.

Int'l. Appln. No. PCT/KR2016/014583A1, Int'l. Search Report and Written Opinion, dated Mar. 14, 2017, 11 pg.

Int'l. Appln. No. PCT/KR2017/002067, Written Opinion, dated May 29, 2017, 7 PG.

Int'l. Appln. No. PCT/KR2017/002039, Int'l. Search Report, dated May 23, 2017, 3 pg.

Int'l. Appln. No. PCT/KR2017/002039, Written Opinion, dated May 23, 2017, 5 pg.

Int'l. Appln. No. PCT/KR2017/002055, Int'l. Search Report and Written Opinion, dated May 29, 2017, 13 pg.

Int'l. Appln. No. PCT/KR2017/002067, Int'l. Search Report, dated May 29, 2017, 7 PG.

U.S. Appl. No. 15/296,689, Restriction Requirement, dated Aug. 28, 2018, 7 pg.

U.S. Appl. No. 15/296,689, Non-Final Office Action, dated Nov. 16, 2018, 12 pg.

U.S. Appl. No. 15/436,920, Notice of Allowance, dated Aug. 29, 2018, 8 pg.

EP Appln. EP16891765.6, Extended European Search Report, Jan. 7, 2019, 9 pg.

EP Appln. EP17756857.3, Extended European Search Report, Jan. 2, 2019, 7 pg.

* cited by examiner

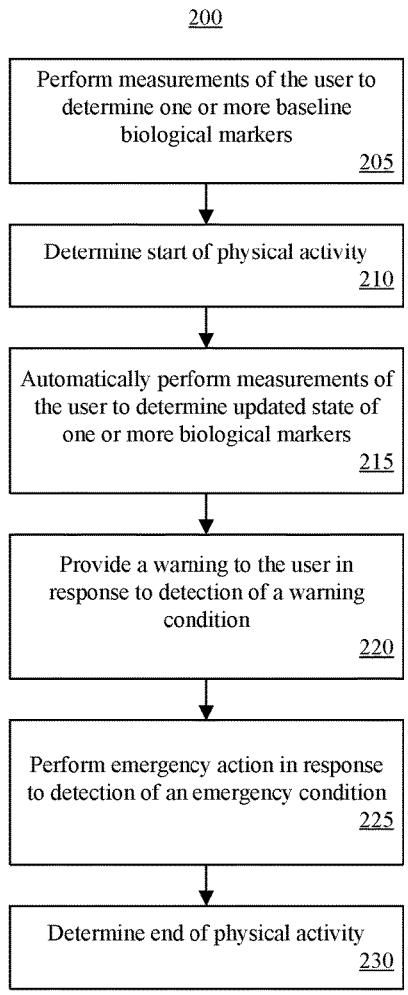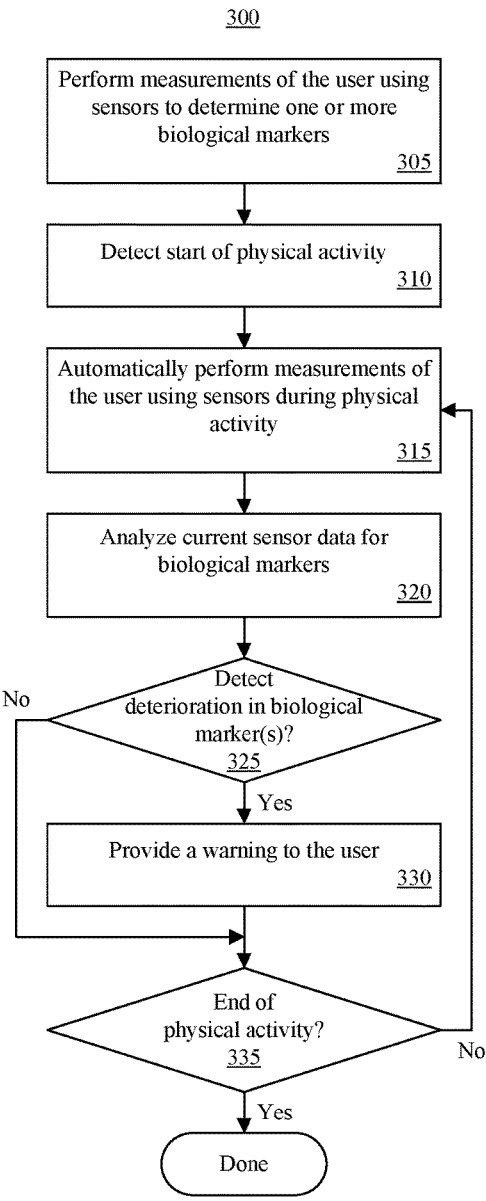
FIG. 2
FIG. 3

SENSOR-BASED DETECTION OF CHANGES IN HEALTH AND VENTILATION THRESHOLD

CROSS-REFERENCE TO RELATED APPLICATIONS

This application claims the benefit of U.S. Provisional Patent Application No. 62/299,960 filed on Feb. 25, 2016, and U.S. Provisional Patent Application No. 62/300,020 filed on Feb. 25, 2016, each being fully incorporated herein by reference.

TECHNICAL FIELD

This disclosure relates to accurate detection of exercise intolerance and ventilation threshold in human beings using sensors and sensor data.

BACKGROUND

Exercise based cardiac rehabilitation has been shown to reduce morbidity and mortality in cardiac patients. Medical guidelines recommend performing cardiopulmonary testing prior to sending a patient home to evaluate the functional capacity of the patient. Such testing, however, is not feasible in many cardiac rehabilitation programs due to a variety of reasons such as, for example, lack of availability of such programs, feasibility for the patient, availability of secondary resources, etc. To the extent that such testing is performed, the exercise prescribed for patients is based largely upon generic heart rate guidelines that are not sufficiently tailored to the individual patient.

In some cases, physicians attempt to account for a patient's individual clinical history and symptoms. For example, a heart rate threshold for a patient may be calculated in a hospital setting for purposes of prescribing exercise. The threshold may be adjusted by the physician based upon the patient's clinical history and/or symptoms by subtracting some number such as 30 beats per minute (BPM) from the heart rate threshold. This manner of calculating heart rate threshold, however, may be overly simplistic and remains firmly grounded in general guidelines. As such, the resulting heart rate threshold does not adequately account for the patient's individual situation.

In addition, heart rate threshold for a patient is subject to change based upon changes in the health status of the patient that occur over time. Some cardiac rehabilitation guidelines, for example, recommend a target heart rate range of 60% to 80% of a predicted maximum heart rate or a 40% to 70% heart rate reserve, combined with a rating of perceived exertion (RPE) of 11-14 on the Borg scale. These quantities may be subject to change. As such, this manner of calculating heart rate threshold may have the undesirable effect of imposing variable metabolic and cardiovascular demands upon the patient.

Further complicating matters, heart rate thresholds that are indicative of exercise intensity often occur at a different percentage of maximal capacity in different patients. Hence, a group of congestive heart failure patients exercising at 50% VO2 max (e.g., the maximum rate of oxygen consumption as measured during incremental exercise) may be working at different relative intensities.

SUMMARY

One or more embodiments are directed to apparatus for monitoring health status of a user. In one aspect, an apparatus includes a sensor adapted to generate sensor data, a memory adapted to store a baseline biological marker for the user, wherein the baseline biological marker includes respiratory rhythm, and a processor coupled to the memory and the sensor. The processor is adapted to, in response to detecting that the user is performing physical activity, determine a biological marker from the sensor data, and compare the biological marker with the baseline biological marker. The processor is adapted to, in response to detecting a change in the biological marker, provide a notification indicating a change in health status.

One or more embodiments are directed to methods of monitoring health status of a user. In one aspect, a method can include determining, using a processor, a baseline biological marker for the user, wherein the baseline biological marker includes respiratory rhythm, receiving, using the processor, sensor data, and, in response to detecting that the user is performing physical activity, determining, using the processor, a biological marker from the sensor data. The method can also include comparing, using the processor, the biological marker with the baseline biological marker and, in response to detecting a change in the biological marker, providing a notification indicating a change in health status.

One or more embodiments are directed to computer program products for monitoring health status of a user. In one aspect, a computer program product includes a computer readable storage medium having program code stored thereon. The program code is executable by a processor to perform executable operations. The executable operations include determining a baseline biological marker for the user, wherein the baseline biological marker includes respiratory rhythm, receiving sensor data, and, in response to detecting that the user is performing physical activity, determining a biological marker from the sensor data. The executable operations can also include comparing the biological marker with the baseline biological marker, and, in response to detecting a change in the biological marker, providing a notification indicating a change in health status.

One or more embodiments are directed to systems and/or apparatus for evaluating ventilation threshold. In one aspect, an apparatus includes a sensor adapted to generate sensor data, a memory adapted to store a baseline RPE, a baseline heart rate, and a biological marker, each corresponding to ventilation threshold for a user, and a processor coupled to the memory and the sensor. The processor is adapted to receive an input specifying an estimate of RPE in response to determining that the sensor data matches the biological marker, determine a current heart for the user from the sensor data in response to determining that the baseline RPE is achieved based upon the input, and compare the current heart rate for the user with the baseline heart rate to detect a change in ventilation threshold for the user. The processor is further adapted to send a notification in response to detecting the change in the ventilation threshold for the user.

One or more embodiments are directed to methods of evaluating ventilation threshold. In one aspect, a method includes determining, using a processor, a baseline RPE, a baseline heart rate, and a biological marker each corresponding to ventilation threshold for a user, receiving, using the processor, an input specifying an estimate of RPE in response to determining that sensor data matches the biological marker, and determining, using the processor, a current heart rate for the user from the sensor data in response to determining that the baseline RPE is achieved based upon the input. The method further includes comparing, using the processor, the current heart rate for the user with the baseline heart rate to detect a change in ventilation threshold for the user and sending a notification in response to detecting the change in the ventilation threshold for the user.

One or more embodiments are directed to computer program products for evaluating ventilation threshold. In one aspect, a computer program product includes a computer readable storage medium having program code stored thereon. The program code is executable by a processor to perform executable operations. The executable operations include determining a baseline RPE, a baseline heart rate, and a biological marker each corresponding to ventilation threshold for a user, receiving an input specifying an estimate of RPE in response to determining that sensor data matches the biological marker, and determining a current heart rate for the user from the sensor data in response to determining that the baseline RPE is achieved based upon the input. The executable operations further can include comparing the current heart rate for the user with the baseline heart rate to detect a change in ventilation threshold for the user and sending a notification in response to detecting the change in the ventilation threshold for the user.

This Summary section is provided merely to introduce certain concepts and not to identify any key or essential features of the claimed subject matter. Many other features and embodiments of the invention will be apparent from the accompanying drawings and from the following detailed description.

BRIEF DESCRIPTION OF THE DRAWINGS

The accompanying drawings show one or more embodiments; however, the accompanying drawings should not be taken to limit the invention to only the embodiments shown. Various aspects and advantages will become apparent upon review of the following detailed description and upon reference to the drawings.

FIG. 2 illustrates an example method of monitoring health status of a user.

FIG. 3 illustrates another example method of monitoring health status of a user.

DETAILED DESCRIPTION

Figure 1:
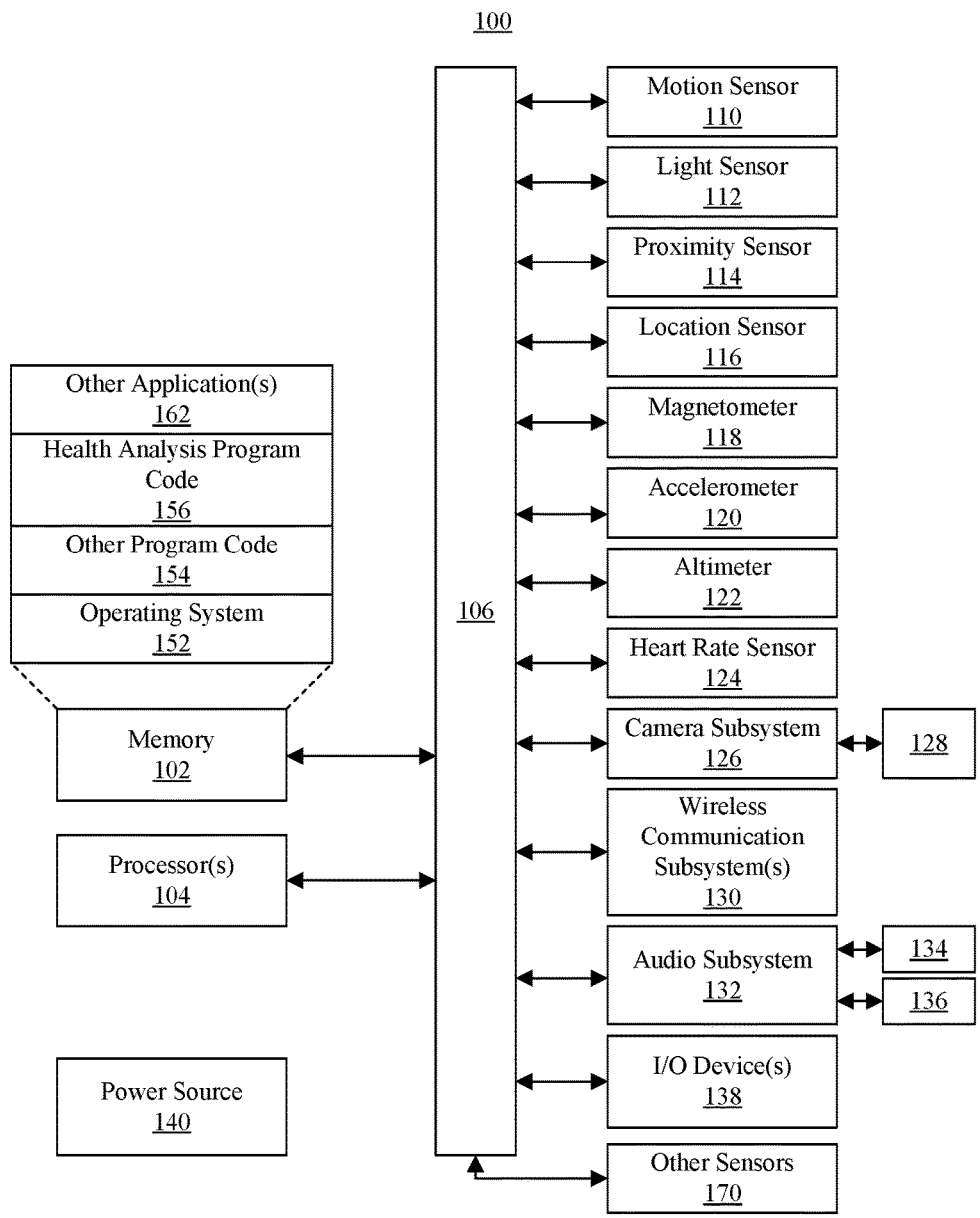
FIG. 1 illustrates an example system in accordance with one or more embodiments described herein.

While the disclosure concludes with claims defining novel features, it is believed that the various features described herein will be better understood from a consideration of the description in conjunction with the drawings. The process(es), machine(s), manufacture(s) and any variations thereof described within this disclosure are provided for purposes of illustration. Any specific structural and functional details described are not to be interpreted as limiting, but merely as a basis for the claims and as a representative basis for teaching one skilled in the art to variously employ the features described in virtually any appropriately detailed structure. Further, the terms and phrases used within this disclosure are not intended to be limiting, but rather to provide an understandable description of the features described.

This disclosure relates to accurate detection of exercise intolerance and ventilation threshold in human beings using sensors and sensor data. In one or more embodiments, a system is adapted to monitor a user using one or more sensors. Sensor data generated by the sensors may be collected over time and in various contexts. For example, the sensor data may be collected while the user is exercising, while the user is in a state of (or has reached) ventilation threshold, while the user is at rest, while the user is sleeping, while the user is engaged in various other activities, etc. The system is capable of analyzing historical sensor data for the user to determine one or more baseline biological markers that may be stored for subsequent use and comparison.

The system is capable of comparing sensor data, e.g., current sensor data, for the user with the baseline biological markers determined from the historical sensor data. For example, the system may determine one or more biological markers from current sensor data that may be compared with corresponding ones of the baseline biological marker(s). The system further is capable of receiving one or more inputs from the user. The inputs may specify subjective data relating to the health of the user. The system is capable of using the comparisons described in combination with the subjective data to detect exercise intolerance and/or ventilation threshold.

In one or more embodiments, the system is capable of detecting confounders. A confounder is a confounding variable or a confounding factor in an unambiguous determination of whether an individual has reached ventilation threshold and/or of whether the ventilation threshold for the user has changed. For example, the system is capable of deciding that a determination that the user has reached ventilation threshold or that the ventilation threshold for the user has changed is suspect when one or more confounders are detected. The confounders may be detected through an analysis of contextual data obtained from sensor data, user input(s), external data sources, etc.

Exercise intolerance refers to a condition where a user is unable to perform physical exercise at a level or for a duration that would be expected of someone in the user's general physical condition. In one or more embodiments, the system is adapted to continue collecting sensor data for the user. The system, for example, may continuously monitor the user using one or more of the sensors. The system is capable of comparing the sensor data, or biological markers determined from the sensor data, with baseline biological markers to determine whether the user is, or has become, exercise intolerant. Within this disclosure, the term "exercise intolerant" is intended to refer to any of a variety of circumstances including, but not limited to, the user exhibiting exercise intolerance from time-to-time, the user acquiring exercise intolerance where the user did not have the condition before, and/or the user having the condition on a temporary basis.

Example embodiments described herein are capable of detecting exercise intolerance in patients with heart failure through evaluation of central limitations, peripheral limitations, and/or reflex limitations using the sensor data. The system is capable of using sensor data to detect biological markers within one or more or each of these different categories in order to detect exercise intolerance. For example, central limitations generally correspond to cardiac output, which may be detected and/or measured using sensor data. Peripheral limitations generally correspond to Endothelial Dysfunction and/or Renin-Angiotensin-Aldosterone System (RAAS), which may be detected and/or measured using sensor data. Reflex limitations generally correspond to Baroreflex Dysfunction and/or Metaboreflex Dysfunction, which also may be detected and/or measured using sensor data.

The system is capable of providing an indication, e.g., a warning, that the user should reduce physical activity in response to determining that the user is or has become exercise intolerant. In one example, the system detects exercise intolerance in response to determining that one or more of the biological markers has deteriorated. The system may determine that the biological marker has deteriorated in response to an analysis. In some cases, the determination that a biological marker has deteriorated is performed relative to the baseline biological marker.

The example embodiments described herein may be used to monitor users that are cardiac patients, are participating in cardiac rehabilitation, and the like. The example embodiments may be used to support or implement a home-based cardiac rehabilitation program. Still, the example embodiments are not intended to be limited solely to individuals with cardiac health issues or individuals in rehabilitation programs. As noted, the example embodiments provided within this disclosure may be used to detect ventilation threshold, changes to ventilation threshold, and/or exercise intolerance in any of a variety of different users, whether ill or not, with varying levels of health to improve fitness.

Further aspects of the inventive arrangements are described below in greater detail with reference to the figures. For purposes of simplicity and clarity of illustration, elements shown in the figures are not necessarily drawn to scale. For example, the dimensions of some of the elements may be exaggerated relative to other elements for clarity. Further, where considered appropriate, reference numbers are repeated among the figures to indicate corresponding, analogous, or like features.

FIG. 1 illustrates an example system 100 in accordance with one or more embodiments described within this disclosure. System 100 can include a memory 102, one or more processors 104 (e.g., image processors, digital signal processors, data processors, etc.), and interface circuitry 106. In one aspect, memory 102, processor(s) 104, and/or interface circuitry 106 are implemented as separate components. In another aspect, memory 102, processor(s) 104, and/or interface circuitry 106 are integrated in one or more integrated circuits. The various components in system 100, for example, can be coupled by one or more communication buses or signal lines (e.g., interconnects and/or wires). In one aspect, memory 102 may be coupled to interface circuitry 106 via a memory interface (not shown).

Sensors, devices, subsystems, and/or input/output (I/O) devices can be coupled to interface circuitry 106 to facilitate the functions and/or operations described within this disclosure including the generation of sensor data. The various sensors, devices, subsystems, and/or I/O devices may be coupled to interface circuitry 106 directly or through one or more intervening I/O controllers (not shown).

For example, motion sensor 110, light sensor 112, and proximity sensor 114 can be coupled to interface circuitry 106 to facilitate orientation, lighting, and proximity functions, respectively, of system 100. Location sensor 116 (e.g., a GPS receiver and/or processor) can be connected to interface circuitry 106 to provide geo-positioning sensor data. Electronic magnetometer 118 (e.g., an integrated circuit chip) can be connected to interface circuitry 106 to provide sensor data that can be used to determine the direction of magnetic North for purposes of directional navigation. Accelerometer 120 can be connected to interface circuitry 106 to provide sensor data that can be used to determine change of speed and direction of movement of a device in 3-dimensions. Altimeter 122 (e.g., an integrated circuit) can be connected to interface circuitry 106 to provide sensor data that can be used to determine altitude. Heart rate sensor 124 can be connected to interface circuitry 106 to generate sensor data and facilitate measurement of a heartbeat and the determination of a heart rate.

Camera subsystem 126 can be coupled to an optical sensor 128. Optical sensor 128 can be implemented using any of a variety of technologies. Examples of optical sensor 128 can include, but are not limited to, a charged coupled device (CCD), a complementary metal-oxide semiconductor (CMOS) optical sensor, etc. Camera subsystem 126 and optical sensor 128 can be used to facilitate camera functions, such as recording images and/or video clips (hereafter "image data"). In one aspect, image data is a subset of sensor data.

Communication functions can be facilitated through one or more wireless communication subsystems 130. Wireless communication subsystems 130 can include, but are not limited to, radio frequency receivers and transmitters, optical (e.g., infrared) receivers and transmitters, and so forth. The specific design and implementation of wireless communication subsystem 130 can depend on the particular type of system 100 implemented and/or the communication network(s) over which system 100 is intended to operate.

For purposes of illustration, wireless communication subsystem(s) 130 may be designed to operate over one or more mobile networks (e.g., GSM, GPRS, EDGE), a WiFi network which may include a WiMax network, a short range wireless network (e.g., a Bluetooth network), and/or any combination of the foregoing. Wireless communication subsystem(s) 130 can implement hosting protocols such that system 100 can be configured as a base station for other wireless devices.

Audio subsystem 132 can be coupled to a speaker 134 and a microphone 136 to facilitate voice-enabled functions, such as voice recognition, voice replication, digital recording, and telephony functions. Audio subsystem 132 is capable of generating audio type sensor data. In one or more embodiments, microphone 136 may be utilized as a respiratory sensor.

I/O devices 138 can be coupled to interface circuitry 106. Examples of I/O devices 138 can include, but are not limited to, display devices, touch sensitive display devices, track pads, keyboards, pointing devices, communication ports (e.g., USB ports), network adapters, buttons or other physical controls, and so forth. A touch sensitive device such as a display screen and/or a pad is configured to detect contact, movement, breaks in contact, etc., using any of a variety of touch sensitivity technologies. Example touch sensitive technologies include, but are not limited to, capacitive, resistive, infrared, and surface acoustic wave technologies, other proximity sensor arrays or other elements for determining one or more points of contact with a touch sensitive device, etc. One or more of I/O devices 138 may be adapted to control functions of sensors, subsystems, and such of system 100.

System 100 further includes a power source 140. Power source 140 is capable of providing electrical power to the various elements of system 100. In an embodiment, power source 140 is implemented as one or more batteries. The batteries may be implemented using any of a variety of different battery technologies whether disposable (e.g., replaceable) or rechargeable. In another embodiment, power source 140 is configured to obtain electrical power from an external source and provide power (e.g., DC power) to the elements of system 100. In the case of a rechargeable battery, power source 140 further may include circuitry that is capable of charging the battery or batteries when coupled to an external power source.

Memory 102 can include random access memory (e.g., volatile memory) and/or non-volatile memory, such as one or more magnetic disk storage devices, one or more optical storage devices, flash memory, etc. Memory 102 can store operating system 152, such as LINUX, UNIX, a mobile operating system, an embedded operating system, etc. Operating system 152 may include instructions for handling system services and for performing hardware dependent tasks.

Memory 102 may also store other program code 154. Examples of other program code 154 may include instructions that facilitate communicating with one or more additional devices, one or more computers and/or one or more servers; graphic user interface processing; sensor-related processing and functions; phone-related processes and functions; electronic-messaging related processes and functions; Web browsing-related processes and functions; media processing-related processes and functions; GPS and navigation-related processes and functions; security functions; camera-related processes and functions including Web camera and/or Web video functions; and so forth. Memory 102 may also store one or more other application(s) 162.

Memory 102 may store health analysis program code 156. In one aspect, health analysis program code 156 is adapted to facilitate detection of exercise intolerance within users. In another aspect, health analysis program code 156 is adapted to facilitate detection of ventilation threshold within users and/or a change to ventilation threshold for users. Health analysis program code 156 is capable of analyzing sensor data, querying a user for input, querying one or more external data sources for information, and performing comparisons of sensor data, user input, and/or data obtained from the external data sources with baseline information. Further aspects of operations performed through execution of health analysis program code 156 are described herein with reference to the remaining figures.

Memory 102 may also store various types of data (not shown) such as sensor data, baseline data including baselines for one or more biological markers, data obtained by way of received user input(s), and/or data obtained by way of querying one or more external data sources.

The various types of instructions and/or program code described are provided for purposes of illustration and not limitation. The program code may be implemented as separate software programs, procedures, or modules. Memory 102 can include additional instructions or fewer instructions. Furthermore, various functions of system 100 may be implemented in hardware and/or in software, including in one or more signal processing and/or application specific integrated circuits.

Program code stored within memory 102 and any data items used, generated, and/or operated upon by system 100 are functional data structures that impart functionality when employed as part of the device. Further examples of functional data structures include, but are not limited to, sensor data, data obtained via user input, data obtained via querying external data sources, baseline information, and so forth. The term "data structure" refers to a physical implementation of a data model's organization of data within a physical memory. As such, a data structure is formed of specific electrical or magnetic structural elements in a memory. A data structure imposes physical organization on the data stored in the memory as used by a processor.

In one or more embodiments, one or more of the various sensors and/or subsystems described with reference to system 100 may be separate devices that are coupled or communicatively linked to system 100 through wired or wireless connections. For example, one or more or all of motion sensor 110, light sensor 112, proximity sensor 114, location sensor 116, magnetometer 118, accelerometer 120, altimeter 122, heart rate sensor 124, camera subsystem 125, audio subsystem 132, and so forth may be implemented as separate systems or subsystems that couple to system 100 by way of I/O devices 138 and/or wireless communication subsystem(s) 130.

One or more of the sensors may be worn directly by the user and provide data to system 100 via a wired or wireless connection. Examples of additional sensors that are not illustrated in FIG. 1, but which may be used and/or worn by a user to provide sensor data to system 100 can include, but are not limited to electrocardiography (ECG) sensors, photoplethysmography (PPG) sensors, gyroscopes, respiratory sensors, galvanic skin response (GSR) sensors, etc. These additional sensors are represented in FIG. 1 by "other sensors" block 170. In one or more embodiments, sensors and/or subsystems as described herein are configured to generate sensor data that is stored in a memory external to system 100. In that case, system 100, e.g., processors 104, may access the sensor data for use and/or analysis as described herein.

System 100 may include fewer components than shown or additional components not illustrated in FIG. 1 depending upon the particular type of system that is implemented. In addition, the particular operating system and/or application(s) and/or other program code included may also vary according to system type. Further, one or more of the illustrative components may be incorporated into, or otherwise form a portion of, another component. For example, a processor may include at least some memory.

System 100 is provided for purposes of illustration and not limitation. A device and/or system configured to perform the operations described herein may have a different architecture than illustrated in FIG. 1. The architecture may be a simplified version of the architecture described in connection with system 100 and include a processor and memory storing instructions. The architecture may include one or more sensors as described herein. System 100, or a system similar to system 100, is capable of collecting data using the various sensors of the device or sensors coupled thereto. It should be appreciated, however, that system 100 may include fewer sensors or additional sensors. Within this disclosure, data generated by a sensor is called "sensor data."

Examples implementations of system 100 may include, but are not to limited to, a smart phone or other mobile device or phone, a wearable computing device (e.g., smart watch, fitness tracker, patch, etc.), a dedicated medical device, a computer (e.g., desktop, laptop, tablet computer, other data processing system, etc.), and any suitable electronic device capable of sensing and processing the sensor data. Furthermore, it will be appreciated that embodiments can be deployed as a standalone device or deployed as multiple devices in a distributed client-server networked system. In an example embodiment, a smart watch or fitness tracker may be paired to operate with a mobile phone. The mobile phone may or may not be configured to interact with a remote server and/or computer system.

In one or more embodiments, a system as described herein in connection with FIG. 1 is capable of continuously monitoring a user using sensors to determine potential states where the user may need to wait or stop before continuing to exercise. These states may occur during cardiac rehabilitation. These states may also occur in various other contexts outside of cardiac rehabilitation. The system may utilize sensor data with calibrated application-user interaction, activity analysis, and contextual information to detect exercise intolerance.

In an embodiment, the system is capable of evaluating various limitations that may cause a change in health status for a user. In an example, the system is capable of detecting exercise intolerance in the user. In one aspect, the system is capable of evaluating central limitations, peripheral limitations, and/or reflex limitations. Central limitations refer to heart, pulmonary, and/or nervous system conditions. Regarding central limitations, the system is capable of evaluating area under the curve in a PPG as an indication of blood pressure, dangerously high heart rate, worsening and/or unexpected arrhythmia, etc.

Peripheral limitations relate to conditions in peripheral organs in the user's body such as muscles other than the heart, arteries, amount of blood flowing through muscles, ECG, etc. Regarding peripheral limitations, the system is capable of analyzing and/or detecting Endothelial ventilation type biological markers such as vascular transit time (VTT), PPG, AUC (area under curve), PEP (pre-ejection period), ECG, etc. For example, the system is capable of evaluating ECG changes such as ST segment elevation, severe dyspnea, hyperventilation, etc. which can be evaluated using techniques well known in the medical literature.

Regarding reflex limitations, the system is capable of evaluating and/or detecting Baroreflex Dysfunction. Regarding Baroreflex Dysfunction, the system is capable of evaluating biological markers such as orthostatic responses. For example, the system is capable of evaluating and/or detecting orthostatic hypertension and/or postural orthostatic tachycardia syndrome (POTS). Orthostatic hypertension is a condition in which a significant increase in the user's blood pressure occurs in response to the user standing up. POTS is a condition in which an abnormally large increase in the user's heart rate occurs in response to the user moving from the supine position to an upright position. Detection of either one of these conditions by the system from sensor data (e.g., accelerometer data, heart rate data and/or blood pressure data from PPG analysis) may trigger a notification to discontinue exercise.

In one aspect, the system is capable of considering negative co-variance between heart rate variability and heart rate with respect to contextual stress with simultaneous deterioration in activity and increase in restlessness and presence of chronotropic incompetence (CI) and disruption in respiratory rhythm. It should be appreciated that contextual stress distinguishes anxiety from depression. Respiratory rhythm refers the regular, oscillating cycle of inspiration and expiration of a user. The normal breathing pattern, e.g., respiratory rhythm, may be altered by a variety of conditions. In this regard, respiratory rhythm may be used to detect suboptimal breathing, which is independent of hyperventilation.

In one or more embodiments, respiratory disturbances can be detected using a machine learning model. An example of a machine learning model is a neural network trained using various respiratory rhythm parameters and executed by the system. The machine learning model may also be extended to other pathologies. In one or more embodiments, the system is capable of detecting exercise intolerance in a user based upon deterioration in a rating of perceived exertion (RPE), deterioration in activity, and detecting disruption in respiratory rhythm.

FIG. 2 illustrates an example method 200 of detecting a change in health status of a user. For example, method 200 may be used to detect exercise intolerance in the user. Method 200 may be implemented using a system as described in connection with FIG. 1. In an embodiment, the system of FIG. 1 is augmented with additional sensors to obtain additional sensor data discussed below such as, for example, ECG, EEG, PPG, and so forth. In another embodiment, the additional sensor data may be collected using one or more other devices and provided to the system for analysis.

In performing method 200, the system is capable of making a determination to discontinue exercise and/or provide a notification to a medical service provider based upon central limitations, peripheral limitations, and/or reflex limitations as described herein. Thus, the entire context of the user is taken into account beyond cardiac output.

In block 205, the system performs measurements, using the sensor(s), of the user to determine one or more baseline biological markers. In one aspect, a baseline biological marker is a historical value, range, pattern, etc., of a biological marker for a user measured under known and/or controlled conditions. In an example, baseline biological markers may be determined while the user is exercising in a controlled environment. While biological markers and/or baseline biological markers may refer to values or ranges from time-to-time herein, it should be appreciated that biological markers and/or baseline biological markers may also refer to time series data. The system is capable of determining a number of different biological markers that may be used as baselines. Examples of biological markers include, but are not limited to, heart rate, heart rate variability, contextual stress, oxygen saturation, hypovolemia, blood pressure, respiratory rate, respiratory rhythm, etc.

In an embodiment, the system is capable of analyzing severe and prolonged contextual stress. The system is capable of generating a baseline for contextual stress. Contextual stress generally corresponds to mental states that may be determined from EEG data analysis. In another embodiment, the system is capable of analyzing hypovolemia based upon PPG waveform analysis. In another embodiment, the system is capable of measuring blood pressure using pulse wave transit time (PWTT). The system is capable of calculating PWTT from sensor data for ECG, phonocardiogram (PCG), or PPG. In another embodiment, the system is capable of analyzing blood pressure by PWTT in simultaneous context of blood volume, contextual psychophysiological stress, medication regime, and medication regimen adherence. Medication regime and adherence may be determined from user entered data tracking medication consumption and/or dose intake.

In another embodiment, the system is capable of measuring respiratory rate and rhythm. The system is capable of determining respiratory rate based upon respiration sensor data, from PPG data alone by using mutual information analysis of the respiratory pattern as indicated by respiratory sinus arrhythmia (RSA) and PPG morphology. The system is capable of monitoring respiratory rate to determine whether the respiratory rate is in a safe range determined by a physician.

In another embodiment, the system is capable of analyzing ventilation threshold using RPE. Ventilation threshold is described herein in greater detail below. In an embodiment, the system is capable of providing a warning or message to the user to take a break from exercise or activity immediately in response to determining that ventilation threshold is reached during any exercise or stress episode.

RPE is a measure of physical activity intensity level. RPE is based upon somatic or psychosomatic sensations related to difficulty of exertion that a user experiences during physical activity which lead to symptoms such as increased heart rate, increased perspiration or breathing rate, increased sweating, muscle fatigue, and so forth. RPE is generally considered a subjective measure of exertion on the part of the user at least when received as a user input in response to querying the user. The device is capable of receiving a user input specifying an RPE value.

In one or more embodiments, the RPE is expressed using the Borg scale. Table 1 below illustrates the scoring of RPE on the Borg scale.

TABLE 1

| Number | Level of Exertion |
| --- | --- |
| 6 | |
| 7 | Very, Very Light |
| 8 | |
| 9 | Very Light |
| 10 | |
| 11 | Fairly Light |
| 12 | |
| 13 | Somewhat hard |
| 14 | |
| 15 | Hard |
| 16 | |
| 17 | Very Hard |
| 18 | |
| 19 | Very, Very Hard |
| 20 | |

In one or more other embodiments, a different scale for measuring RPE may be used. In this regard, the inventive arrangements are not intended to be limited to using one particular scale for RPE. It should be appreciated that in an effort to ensure consistent results, patients may be trained in estimating activity level using an appropriate scale. For example, within a hospital setting, in a rehabilitation setting, or anywhere working with trained medical staff, the patient may be instructed in how to properly estimate activity level using the selected scale.

In one example, the user is instructed as to how to rate RPE using the Borg scale. For example, trained medical personnel may provide instruction to the user while the user is at a hospital or another medical facility. In another example, trained medical personnel may provide instruction to the user through a communication channel such as via a telephone call, a video call, or the like while the user is monitored remotely. The user, for example, may be monitored using tele-monitoring or another remote monitoring technology including an Internet or Web-based monitoring technology.

In block 210, the system is capable of determining a start of physical activity. In an embodiment, the system is capable of receiving a data from a user as provided input through a user interface generated by the system. The data indicates that exercise has started. In another embodiment, the system is capable of automatically detecting the start of exercise based upon accelerometer data, motion or location tracking sensor data, etc., indicating that the user is engaged in particular movements identified by the system as exercise(s).

In another aspect, the system is capable of checking for supine heart rate in the user in the case where exercise is to be started. If, for example, supine heart rate is above 100 beats per minute (BPM), the system is capable of providing a warning that exercise should not be started. If exercise is still initiated, the system may consider a severe heart rate elevation episode as an overload on the cardiopulmonary system of the user.

In block 215, the system is capable of continuing to perform measurements of the biological markers throughout performance of the physical activity of the user. In doing so, the system determines updated states for the various biological markers for which baselines are determined. The system is capable of continuing to measure biological markers to monitor for warning conditions and/or emergency conditions.

In block 220, the system is capable of providing a warning to the user in response to detecting a warning condition. The warning can be a visual, audible, and/or audiovisual notification that the user has entered into a warning condition and that the user should rest. In an embodiment, when the system detects the end or termination of a warning condition, the system is capable of notifying the user that resuming physical activity is safe again.

In an embodiment, the system is capable of analyzing covariance of one or more or of each of the biological markers discussed above with respect to the corresponding baseline. For example, the system is capable of analyzing covariance of severe and prolonged contextual stress, oxygen saturation, hypovolemia, change in blood pressure in particular context(s) (e.g., orthostatic response), and/or respiratory rate and rhythm with respect to arrhythmia, ECG changes, and/or dyspnea. If the system determines that the co-variance is unexpected and is unhealthy, e.g., differs from a baseline biological marker by more than a threshold amount, the system is capable of flagging the covariance as a warning condition.

For example, the system is capable of analyzing relative changes in blood pressure. The system is capable of determining whether blood pressure had deteriorated. Further, the system is capable of analyzing blood pressure by PWTT in simultaneous context of blood volume, contextual psychophysiological stress, medication regime, and medication regimen adherence. Medication regime and adherence may be determined from user entered data tracking medication consumption and/or dose intake.

In another example, the system is capable of analyzing respiratory rate and rhythm. The system is capable of analyzing respiratory rate using mutual information. For example, the system is capable of analyzing respiratory rhythm using PPG data alone by using mutual information analysis of the respiratory pattern as indicated by respiratory sinus arrhythmia (RSA) and PPG morphology. The system is capable of monitoring respiratory rate to determine whether the respiratory rate is in a safe range determined by a physician.

The system is also capable of detecting additional warning conditions as described herein. In another example, the system is capable of detecting a warning condition in response to determining that, once exercise has begun, PPG morphology has shifted toward a lower blood pressure. In that case, the system is capable of providing a warning such as a sound indicating that exercise should be stopped immediately.

In another example, the system is capable of detecting a warning condition in response to detecting an exertion where the target heart rate of the user exceeds a limit imposed by ventilation threshold. If, for example, the heart rate exceeds ventilation threshold heart rate for the user, the user is at risk of entering the dangerous state of respiratory compensation in which the risk of cardiac events increases significantly. In that case, the system is capable of generating a warning such as a sound in response to the heart rate of the user being above the ventilation threshold associated heart rate by a threshold amount. The threshold amount may be 10 BPM or another value less than 10 BPM or greater than 10 BPM. Another example warning condition can include the system determining that heart rate of the user is above the ventilation threshold heart rate (e.g., the baseline heart rate) and also near, e.g., within a percentage or predetermined amount, of respiratory compensation.

In block 225, the system is capable of performing an emergency action in response to detection of an emergency condition. An emergency action can include a notification indicating the severity of the condition and/or automatic data communication to a server of an emergency service provider. Example emergency conditions can include severely high contextual stress (e.g., as determined from low heart rate variability), severely high contextual stress with low resilience. Low resilience may be calibrated using a baseline and corresponds to mental states as determined by EEG analysis. Other example emergency conditions include severe dyspnea that leads to significant ceasing of physical activity and lower trending blood pressure despite no antihypertensive medication taken in the immediate past.

In an embodiment, the system is capable of performing an emergency action in response to detecting any one or more of the emergency conditions. In another embodiment, in response to the system detecting all of the example emergency conditions, the system determines that the user's situation is very urgent and that immediate medical attention should be sought. The system may send a notification to a medical service provider indicating that the user is in need of medical attention.

In another embodiment, the system may prompt the user as to how the user feels, e.g., fine or not. Prompting the user as described may be implemented to reduce the likelihood of a false positive emergency condition. The emergency condition may be further exacerbated in the event the system detects an onset of arrhythmia. For example, the system is capable of prompting the user by asking one or more pre-programmed questions. The questions may be commensurate with the user's education level in order to assess or test the user's cognitive state.

In block 230, the system may determine the end of physical activity. In one example, the system is capable of automatically detecting the end of physical activity based upon sensor data such as accelerometer data, motion or location tracking sensor data, etc. In another example, the user may provide a user input indicating that physical activity has been discontinued or stopped.

FIG. 3 illustrates another example method 300 of monitoring health status of a user. In an aspect, method 300 is capable of detecting a change in health status of a user which may include, but is not limited to, exercise intolerance. Method 300 may be performed using a system as described herein in connection with FIG. 1. In an embodiment, the system of FIG. 1 is augmented with additional sensors to obtain additional sensor data discussed below such as, for example, ECG, EEG, PPG, and so forth. In another embodiment, the additional sensor data may be collected using one or more other devices and provided to the system for analysis.

In performing method 300, the system is capable of making a determination to discontinue exercise and/or provide a notification to a medical service provider based upon central limitations, peripheral limitations, and/or reflex limitations as described herein. Thus, the entire context of the user is taken into account beyond cardiac output.

In block 305, the system is capable of performing measurements, using the sensor(s), of the user to determine one or more baseline biological markers. Examples of biological markers determined by the system from sensor data can include, but are not limited to, RPE, stress to the left ventricle wall of the user's heart as indicated by ventilation threshold, heart rate, heart rate variability (determined from PPG and/or ECG sensor data), movement of the user from accelerometer data, respiratory control system state, etc. The system is capable of generating a baseline biological marker for one or more or each of the biological markers described herein.

It should be appreciated that the system is capable of determining the various biological markers described herein with reference to FIGS. 2 and/or 3. As such, while one or more biological markers described with reference to FIG. 2 may not be specifically mentioned in describing FIG. 3, the system is capable of determining and evaluating such biological markers in the context of performing method 300.

In block 310, the system is capable of detecting a start of physical activity for the user. In an embodiment, the system detects the start of physical activity for the user based upon accelerometer data, motion or location tracking data, etc. indicating that the user is active or engaging in particular movements indicative of exercise. In another example, the system is capable of receiving data via a user input indicating that the user is starting physical activity. As discussed, the system is capable of checking supine heart rate as described previously in connection with FIG. 2 and issuing notifications as described.

In block 315, the system is capable of continuing to perform measurements of the user using sensors during physical activity. In block 320, the system is capable of analyzing the current sensor data to determine one or more of the biological markers, e.g., a current or updated state of the biological markers.

In block 325, the system determines whether one or more of the biological markers has deteriorated. In an aspect, deterioration of a biological marker is when the biological marker, e.g., the current or updated state of the biological marker, has deteriorated or degraded by more than a predetermined or threshold amount compared to the corresponding baseline biological marker. Deterioration of one or more of the biological markers is considered a warning condition for the system and a change in health status of the user. For example, one or more of the biological markers discussed may be considered acute.

In one aspect, the system is capable of comparing the biological markers determined from real time sensor data during exercise with the previously established baseline biological markers. For example, the system is capable of analyzing accelerometer data to measure movement of a user throughout the day, e.g., performing day-to-day activities such as going to the store, doing housework, etc. A decrease in movement compared to the baseline indicates that the user is not able to move around much during the day. In one or more embodiments, the system is capable of determining whether there is a decrease in the movement(s)

of the user for two or more days, e.g., more than a threshold amount of time. The system is capable of detecting a decrease in the movement(s) of the user responsive to determining that the movements of the user, per the accelerometer sensor data (e.g., power output) have decreased or are consistently lower compared to a baseline level of movement for the user for a minimum time period, e.g., several days. In another aspect, the system may ensure that during the time period, no physiological and/or psychological confounders are detected.

In one or more embodiments, the system is capable of evaluating the respiratory control system of the user using biological markers such as respiratory rhythm, respiratory depth (e.g., volume), and/or respiratory rate (e.g., breaths per minute or unit time). The system is capable of comparing the respiratory biological markers with baseline respiratory biological markers to determine whether one or more of the respiratory biological markers has deteriorated, e.g., varies by more than a threshold amount from the corresponding baseline biological marker.

In another aspect, the system is capable of evaluating biological markers using machine learning. The machine learning may receive sensor data indicating context of the user, e.g., activity as may be determined from accelerometer data; respiratory rhythm, respiratory depth, and/or respiratory rate as may be determined from a respiratory sensor; heart rate; heart rate variability; PPG data indicating blood pressure; and/or ECG data. The system is capable of applying machine learning to the biological markers to determine a likelihood that the health status of the user has deteriorated such that the user should no longer exercise. For example, a trained neural network executed by the system may receive the aforementioned data as input and generate a probability that the health status of the user has decreased (or increased as the case may be).

Other deteriorations in biological markers detectable by the system include, but are not limited to, a decline in RPE, detection of reduced ventilation threshold, inappropriate heart rate (e.g., heart rate higher than predetermined threshold), inappropriate heart rate variability response to exertion as indicated using PPG and/or ECG sensor data (e.g., a heart rate variability lower than an expected heart rate variability), and lack of proper rhythm in respiration. A change in RPE may be determined using any of the various techniques described herein. Regarding respiratory rhythm, in an aspect, improper respiratory rhythm may be detected by applying frequency domain-based signal processing techniques on respiration data obtained from respiration sensors. The system is capable of determining that the respiration rhythm varies from a proper or expected (e.g., a baseline) respiratory rhythm by at least a predetermined amount. Further, the system is capable of detecting a suboptimal respiration pattern, e.g., one that varies as described, in the user independently of hyperventilation in the user based upon sensor data from the respiration sensor(s).

In response to determining that one or more of the biological markers has deteriorated for the user, method 300 continues to block 330. In response to determining that the biological markers have not deteriorated, method 300 continues to block 335.

In block 330, the system is capable of providing a warning to the user. The warning may indicate that the user should discontinue physical activity. The warning further may indicate the particular biological markers found to have deteriorated. In one or more embodiments, the system may also send a notification to a remote data processing system such as a server for a medical service provider or the like.

In block 335, the system is capable of detecting whether the user has ended physical activity. The system is capable of determining whether the user has ended physical activity by analyzing accelerometer data (e.g., an automated detection), by receiving a user input indicating that physical activity has been discontinued, or the like.

In one or more embodiments, the system is capable of detecting changes such as improvements in the biological markers described herein relative to the baselines. The system is capable of sending notifications indicating the detected change, whether a deterioration or an improvement, in one or more of the various biological markers discussed.

Ventilation threshold generally refers to the point at which a transition from moderate sustainable exercise to heavy exercise occurs for an individual. Ventilation threshold is effectively the transition point between an aerobic metabolism and an anaerobic metabolism. When a user exercises above the ventilation threshold, the user may experience increased stress. This may be particularly true in the case of heart patients including heart failure patients.

In an embodiment, the system is capable of determining whether ventilation threshold for the user changes. In this regard, the system is capable of determining whether an improvement in ventilation threshold for the user is detected or whether a deterioration in ventilation threshold for the user is detected. Such determinations, e.g., improvement, remaining the same, or deteriorating, allow the user to optimize the training or rehabilitation regimen being performed. Thus, changes in ventilation threshold may be used by persons that are ill and persons that are not ill, but wish to improve fitness and/or physical prowess.

In one or more embodiments, the system is adapted to perform validation as to any determinations relating to ventilation threshold. The system is capable of utilizing sensor data in order to ensure that the user has reached ventilation threshold and/or that the ventilation threshold of the user has changed in some way. The system is capable of sending a notification to a remote data processing system. The notification may be sent in response to detecting the ventilation threshold for the user, determining that the ventilation threshold for the user has changed, or in other circumstances as described herein.

Figures 4, 5:
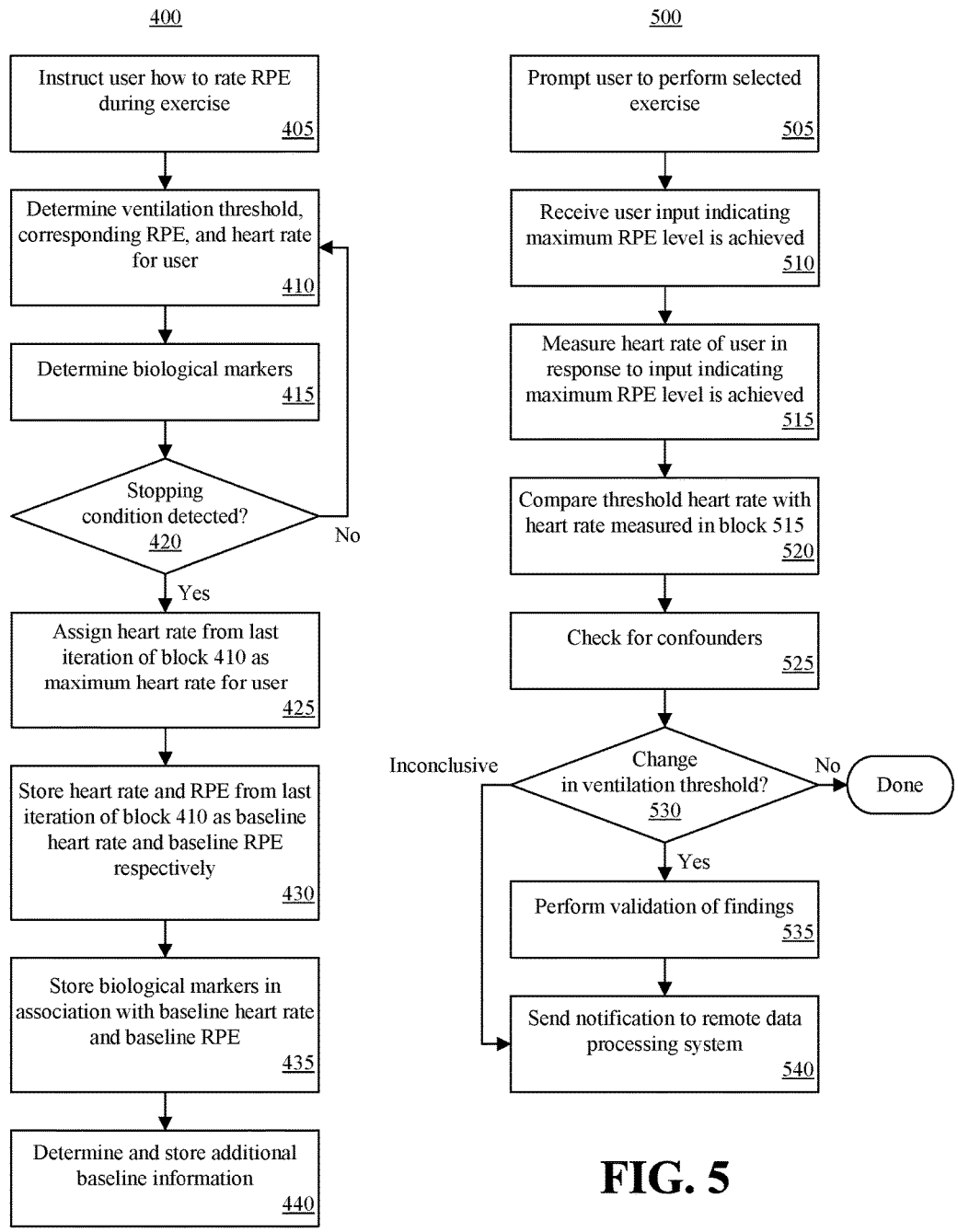
FIG. 4 illustrates an example method of implementing a calibration phase for collecting data for a user.
FIG. 5 illustrates an example method of evaluating ventilation threshold.

FIG. 4 illustrates a method 400 of implementing a calibration phase for collecting data for a user. In an embodiment, the data that is collected may be used in detecting ventilation threshold and/or a change in ventilation threshold for a user. In one or more embodiments, method 400 is implemented using a system such as the system described in connection with FIG. 1. In an embodiment, method 400 is implemented using another system such as a cardiopulmonary testing system, where the resulting data is stored and made available to a system as described in connection with FIG. 1.

In block 405, the user is instructed how to rate or estimate an RPE during exercise as previously described herein.

In block 410, the ventilation threshold, the corresponding RPE, and the corresponding heart rate for the user are determined. For example, the user may be outfitted with one or more sensors including a heart rate sensor. The sensor may be coupled to a system such as a cardiopulmonary testing system that is capable of directly determining ventilation threshold for the user using available sensor(s). When the user reaches, or approximately reaches, ventilation threshold, the system is capable of measuring the heart rate of the user at that time. In addition, the system is capable of receiving an input from the user specifying an estimated RPE value. The system is capable of storing the heart rate of the user and the estimated RPE of the user, where each corresponds to ventilation threshold of the user.

In block 415, the system optionally determines one or more biological markers in response to the user reaching ventilation threshold. In one or more embodiments, the system is capable of storing respiratory sound, e.g., a respiratory waveform, of the user in response to the user reaching ventilation threshold. The respiratory sound may be obtained using a sensor such as a microphone or a respiratory sensor. The respiratory sound may be stored with, or in association with, the heart rate and RPE corresponding to ventilation threshold for the user. Thus, the respiratory sound of the user upon reaching ventilation threshold may be stored and used as a biological marker.

In an embodiment, the system is capable of storing a measure of total energy expended in response to the user reaching ventilation threshold. The total energy may be determined using an accelerometer where the total amount of energy expended by the user may be measured as the output wattage from the accelerometer for the time period over which the user exercises to reach ventilation threshold. The total energy expended by the user upon reaching ventilation threshold may be stored and used as a baseline biological marker.

In block 420, the system is capable of determining whether a stopping condition is detected. If so, method 400 may continue to block 425. If not, method 400 may loop back to block 410 to continue. The determination of the ventilation threshold, the heart rate, and the estimated RPE for the user may be repeated until the stopping condition is reached. In the case where biological markers such as respiratory sound and/or total energy expended are recorded, these biological markers may also be determined for each iteration of block 410.

For example, the system is capable of prompting the user to perform an exercise without the user being informed that the user is about to reach ventilation threshold. In response to detecting that the user is approximately at the ventilation threshold, the system can prompt the user to obtain an estimate of the RPE value specified on the Borg scale. Further, the system is capable of again measuring the heart rate of the user from sensor data at that time and/or the biological markers noted above.

An example of a stopping condition is where the user is able to correctly and consistently assess the estimated RPE value of the user's ventilation threshold. For instance, a stopping condition is satisfied, or detected, when the difference between a predetermined number of consecutive estimated RPE values is below a threshold value. In another example, a stopping condition is satisfied when the mean square error of a predetermined number of estimated RPE values is less than a threshold value.

In block 425, the system is capable of assigning the heart rate determined in the last iteration of block 410 as the maximum heart rate for the user. Further, the system is capable of setting the target heart rate for the exercise to the maximum heart rate and/or a percentage thereof.

In block 430, the system is capable of storing the heart rate from the last iteration of block 410 as the baseline heart rate or an average of the last N heart rate measurements found to meet the stopping condition as the baseline heart rate (where N is an integer value corresponding to the predetermined number of consecutive estimated RPE values described above). The system is also capable of storing the RPE from the last iteration of block 410 as the baseline RPE or an average of the last N RPE values. The baseline heart rate and the baseline RPE are for, or correspond to, ventilation threshold of the user, e.g., as opposed to being for the user at rest or in another context.

In block 435, the system optionally stores the biological marker(s) determined in block 415. In one aspect, the system is capable of storing the biological markers determined in the last iteration of block 415 for ventilation threshold or an average of the last N iterations of block 415 for one or both of the biological markers.

In block 440, the system optionally determines and stores data relating to the context of the user. The data may be used to determine or detect the presence of confounders at a later time. Examples of data that may be stored include, but are not limited to, activity level, homeostatic disturbances, cardiac pathology, pulmonary pathology, musculoskeletal issues, environment, altitude, weather, hydration, etc.

For example, environment data such as particulate pollution level for the location of the user during testing may be determined and stored with the ventilation threshold of the user as part of the baseline data. The altitude and weather for the location of the user during testing may be determined and stored with the ventilation threshold as additional baseline data. Other examples of baseline data may be collected over time and reflect the general health and/or state of the user as opposed to the state of the user while exercising. For example, activity level, homeostatic disturbances, cardiac pathology, pulmonary pathology, musculoskeletal issues may be determined during normal or resting circumstances and stored as baseline data for the user.

In one or more embodiments, the system is capable of storing heart rate recovery data for the user as additional baseline data. For example, the heart rate recovery of the user, e.g., the change in heart rate for the user post exertion or after reaching ventilation threshold, may be recorded, e.g., as a time series of data, and used as a baseline for later comparison. In one or more embodiments, heart rate recovery is used by the system as a validation mechanism for ensuring that ventilation threshold has occurred and/or has changed.

FIG. 5 illustrates an example method 500 of evaluating ventilation threshold and/or a change in ventilation threshold for a user. FIG. 5 illustrates a real time method of detecting ventilation threshold or a change in ventilation threshold for a user that utilizes data as described and collected with reference to FIG. 4. In an embodiment, method 500 is performed by a system as described with reference to FIG. 1.

In block 505, the system prompts the user to perform a selected exercise. For example, the system may play an audio prompt or display a message using a user interface prompting the user to begin exercising. In addition, the system is capable of instructing the user to perform the exercise and to provide an indication when the user believes that the maximum RPE level is achieved. For example, during exercise at home, at a gym, in an unsupervised setting, etc., the system is capable of prompting the user to initiate an exercise and to achieve a maximum RPE level for the exercise.

With the user starting to exercise, the system is capable of monitoring the user using one or more of the sensors described herein. For example, the system is capable of performing health monitoring as the user exercises. The system is capable of monitoring the user's heart rate using the heart rate sensor to generate a time series of sensor data. The system is also capable of monitoring other physiological and/or health indicators while the user exercises.

In block 510, the system receives a user input indicating that the maximum RPE level for the user is reached. In an embodiment, the system is capable of providing a user interface through which data may be received from the user. The data is indicative of the user achieving the user's maximum RPE level. The data may specify a particular RPE value.

In block 515, in response to receiving a user input indicating that the maximum RPE level is achieved for the user, the system measures the heart rate, or determines the heart rate of the user from current sensor data. The system is capable of measuring the user's heart rate and/or other physiological indicators in real time.

In block 520, the system is capable of comparing the previously stored baseline heart rate of the user with the heart rate measured in block 515, e.g., when the user indicated that the maximum RPE level was achieved. The system compares the current heart rate to the baseline heart rate, which is the heart rate for the user at ventilation threshold.

In block 525, the system is capable of checking for one or more confounders. Examples of confounders include, but are not limited to, any of a variety of behaviors, medical conditions, or other data items that define a context for the individual. In one aspect, confounders are classified as either physiological or external. Examples of physiological confounders include activity level, homeostatic disturbances, cardiac pathology, pulmonary pathology, and musculoskeletal issues. Examples of external confounders include one's environment, altitude, weather, and hydration. Confounders and the detection of confounders are described in greater detail following the discussion of FIG. 5.

In block 530, the system is capable of determining whether a change in the ventilation threshold for the user is detected. The system is capable of detecting a change in ventilation threshold for the user based upon the comparison performed in block 520. For example, the system is capable of determining whether the heart rate measured in block 515, e.g., the current heart rate, is higher, lower, or the same as the baseline heart rate.

If, for example, the current heart rate for the user, as determined during exercise, is lower than the baseline heart rate corresponding to ventilation threshold for the user, the system determines that the ventilation threshold has changed and, in particular, has decreased (e.g., improved). In one or more embodiments, the system is capable of replacing the baseline heart rate associated with ventilation threshold with the current heart rate for future comparisons.

If, for example, the current heart rate for the user, as determined during exercise, is higher than the baseline heart rate corresponding to ventilation threshold for the user, the system determines that the ventilation threshold has changed and, in particular, has increased (e.g., worsened). In one or more embodiments, the system is capable of replacing the baseline heart rate associated with ventilation threshold with the current heart rate for future comparisons.

If, for example, the current heart rate for the user, as determined during exercise, is the same as the baseline heart rate corresponding to ventilation threshold for the user, the system determines that the ventilation threshold has been reached and is unchanged. In one or more embodiments, the system is capable of maintaining the baseline heart rate associated with ventilation threshold for future comparisons.

In one or more embodiments, the system determines whether a change in ventilation threshold occurs based upon detecting an increase (decrease) above (below) a threshold amount. For example, the system is capable of determining that the user's heart rate increased or decreased as the case may be only when the difference from the baseline heart rate at ventilation threshold differs by more than the threshold amount.

Accordingly, if the system detects no change in ventilation threshold, method 500 can end. If the system detects a change in ventilation threshold, method 500 can continue to block 535. If the system determines that the change in ventilation threshold is inconclusive, method 500 can proceed to block 540. For example, if the system detects one or more confounders, the system determines that the ventilation threshold determination, whether increased, decreased, or the same, is inconclusive. More particularly, when the system detects one or more confounders in combination with reduced or increased heart rate, the system is unable to attribute the change in heart rate to a change in ventilation threshold.

In block 535, the system is capable of performing validation. The system is capable of validating a determination that a change in ventilation threshold has occurred for the user. In one aspect, the system is capable of using Respiratory Sinus Arrhythmia (RSA) for purposes of validating a determination that the ventilation threshold has changed. In the case where the system detects a rising heart rate, to remove the confounder effect, the system is capable of checking the magnitude of RSA during inspiration/expiration during exercise. This is because the heart rate naturally increases during the inspiration period, and decreases during the expiration period. Thus, it is important to compare only the corresponding phases in the baseline data and the test data. For example, as compared to the heart rate in the baseline time series of the heart rate data, if for the same effort level in the time series of heart rate test data, and same phase in RSA cycle (inspiration or expiration), the RPE for ventilation threshold (e.g., RPE=14) corresponds to a significantly higher or lower heart rate, then that is an indication that the ventilation threshold may have changed. In response to the system detecting this condition consistently over several sessions, the system determines that the ventilation threshold has changed. A lowering of the heart rate indicates improvement in ventilation threshold and increase in heart rate indicates worsening of the ventilation threshold.

In another aspect, the system is capable of using heart rate recovery for purposes of validating a determination that the ventilation threshold has changed. For example, in the case of detecting an increase in heart rate, the new RPE to heart rate relationship and the implication of a heart rate increase can be validated during the heart rate recovery component part of the heart rate time series of sensor data. If, for example, the higher heart rate is achieved by the user getting deep into the anaerobic threshold, the user will have a relatively (relative to the baseline case) activated sympathetic nervous system (SNS) during heart rate recovery. This phenomenon can be detected as a relatively reduced heart rate variability as compared to the baseline heart rate variability that may be stored as part of the baseline data for the user.

Regarding heart rate recovery, for example, the system is capable of determining whether the heart rate recovery is bi-exponential from the heart rate sensor data. A person's heart rate recovers from a maximum heart rate during exercise to a heart rate at rest at a rate of $e^{-kt}$ The system is capable of continuing to monitor heart rate for the user during recovery from exercise. The system is capable of fitting a curve to the heart rate recovery data for the user. A person of lesser health tends to have a more linear heart rate recovery. The system is capable of fitting a curve to the time series of heart rate data for the user to determine a value of "k." In one or more embodiments, the system is capable of validating an increase or improvement in fitness by detecting an increase in the value of k compared to a baseline heart rate recovery for the user. Conversely, the system is capable of validating a decrease or reduction in fitness by detecting a decrease in the value of k compared to a baseline heart rate recovery for the user. Determination of increase or decrease in fitness can act as a check to validate any ventilation threshold determination.

In block 540, the system is capable of sending a notification to a remote data processing system. The remote data processing system may be for a medical provider for the user. In one aspect, the system is capable of sending a notification that the ventilation threshold has changed. The notification may include the newly determined ventilation threshold. In one or more embodiments, the ventilation threshold may be specified in watts of power required for the user to reach ventilation threshold. In another aspect, the notification can specify or include sensor data, e.g., current sensor data such as heart rate. In another aspect, in the case where the determination of whether a change in ventilation threshold has occurred is inconclusive, the notification can specify any confounders that were detected within the sensor data.

In one or more embodiments, the notification can specify the corresponding health-related changes and causalities. Examples of such information provided to the remote data processing system can include sensor data or user inputs indicating lack of exercise compliance, changes in medication or lack of medication regimen adherence, tobacco consumption, higher fluid consumption, progressive decrease in sleep, increase in depression, etc. This information can facilitate assessing the potential causality of the degradation in health.

In one or more embodiments, the system is capable of replacing the target heart rate if the RPE level reached during this exercise is lower than the RPE level determined as described in connection with FIG. 4. The replacement of the target heart rate, however, may be omitted.

As discussed, confounders relating to the detection of ventilation threshold and/or a change thereto may be physiological and/or external. The detection of a confounder while attempting to detect a change in ventilation threshold renders the detection inconclusive. The inventive arrangements described herein therefore are able to utilize wearable sensors to implement a conservative methodology for detecting changes in ventilation threshold that avoids providing notifications and/or warnings of worsening ventilation threshold in cases where confounders are detected.

Examples of physiological confounders include, but are not limited to, activity level, homeostatic disturbances, cardiac pathology, pulmonary pathology, and musculoskeletal issues. In one or more embodiments, the system is capable of detecting the presence of physiological confounders from the sensor data. The system is capable of ascertaining whether such confounders exist. In an aspect, the system is capable of determining that a confounder exists where a confounder is detected that was not detected within historical data. In another aspect, the system is capable of determining that a confounder exists where a confounder that did exist within the baseline data is found to deviate (e.g., deteriorate) compared to baseline and/or historical data.

Detecting lower or higher activity levels for the user immediately prior to the start of the ventilation threshold analysis are considered confounders. Regarding activity level, for example, the system is capable of monitoring activity level of the user from accelerometer data. The system may determine activity level based upon the power, e.g., wattage, generated by an accelerometer over time. Power output of the accelerometer may be used in place of estimates of the number of steps taken by the user. The system is capable of evaluating the user's walking or running speed, for example. In another example, the system is capable of detecting that the user has been climbing stairs in the recent past, e.g., prior to exercising.

The overall activity level may be compared with an activity level established for the user in the baseline data. In one or more embodiments, the system is capable of monitoring overall activity of the user for periods of time during which the user is not exercising. For example, the system is capable of detecting overall activity over extended periods of time and/or while the user is performing daily tasks. The system may detect a confounder in response to determining that the activity level of the user during a period immediately prior to the start of exercise is reduced compared to the baseline activity level for the user. As another example, the system may detect a confounder in response to determining that the activity level of the user during a period immediately prior to the start of exercise is increased compared to the baseline activity level for the user thereby indicating that the user is starting exercise already having performed a potentially strenuous activity and/or is more tired than usual.

Regarding homeostatic disturbances, for example, the system is capable of using sensor data to detect exposure of the user to stress, to detect sleep quality (e.g., sleep deprivation), etc. When under stress, for example, the user's Autonomic Nervous System (ANS) arousal and valence are typically in the second quadrant of the Circumplex Model of Emotions, which can be determined by heart rate and heart rate variability analysis where both trend down at the same time. In an embodiment, the system is capable of using heart rate and/or heart rate variability from the sensor data to determine whether the user is under stress and/or the amount of stress.

For example, the system is capable of determining whether the user is subject to stress and whether the amount of stress exceeds a baseline amount of stress based upon heart rate (e.g., energy) and heart rate variability (e.g., mood) of the user both being low (e.g., below a baseline for heart rate and/or a baseline for heart rate variability) at the same time and/or remaining low (concurrently) for at least a minimum amount of time. The baseline(s) may be specific to the user or generalized across one or more different users. Responsive to determining that the heart rate and heart rate variability both are low for at least the minimum amount of time immediately prior to exercise, for example, the system determines that the user is experiencing a higher than normal amount of stress, which the system considers a confounder.

In another example, the system is capable of detecting, from the sensor data, the confounder of sleep deprivation. For example, the system is capable of measuring sleep of the user using heart rate data and accelerometer data. The system is capable of determining the amount of time that the user sleeps and comparing the amount of time spent sleeping with a baseline amount of time (whether personal to the user or a generalized baseline determined across one or more other users) to determine sleep deprivation for the user. In one or more embodiments, the system is capable of monitoring sleep quality (e.g., sleep deprivation) for periods of time where the user is not exercising. For example, the system is capable of detecting sleep deprivation over extended periods of time including immediately prior to the start of exercise, which the system considers a confounder.

Regarding cardiac pathology, for example, the system is capable of detecting whether the user is chronotropically incompetent. Chronotropic incompetence (CI), broadly speaking, is the inability of the heart to increase its heart rate commensurate with increased activity or demand. The system is capable of detecting CI by monitoring sensor data and/or received user inputs over a period of time. Detection of CI is described in greater detail in connection with FIGS. 7, 8, and 9. CI is a confounder for detecting a change in ventilation threshold.

Regarding pulmonary pathology, for example, the system is capable of looking up user provided health history data to determine whether the user suffers from chronic obstructive pulmonary disease (COPD). COPD is a confounder for measuring ventilation threshold.

Regarding musculoskeletal issues, for example, the system is capable of using sensor data to determine whether the user suffers from joint problems. The system is capable of using accelerometer data to analyze the gait of the user. The system is capable of determining whether the user suffers from one or more joint problems based upon the gait analysis that is performed. The system is capable of determining that a musculoskeletal confounder exists in response to detecting a joint problem where such a joint problem did not exist within the baseline data. In another example, the system is capable of determining that a musculoskeletal confounder exists in response to detecting that a joint problem that existed in the baseline data has become worse. In one or more embodiments, the system is capable of monitoring for joint problems for periods of time during which the user is not exercising including the time immediately prior to the start of exercise. For example, the system is capable of detecting joint problems over extended periods of time and/or while the user is performing daily tasks.

Examples of external confounders include, but are not limited to, environment, weather, altitude, and hydration. In one or more embodiments, the system is capable of detecting the presence of external confounders from the sensor data, by querying one or more external data sources, and/or using user inputs that log user activities.

Regarding environment, for example, the system is capable of querying an external data source that lists environmental factors such as particle pollution (also referred to as particulate matter (PM)) based upon location. As used within this disclosure, the term "external data source" refers to an Internet-based or Web-based service or Website that may be queried for particular information. The system, for example, may include location data or obtain location data using GPS or another location determination technique, e.g., using WiFi networks, and query the external data source for the PM of the user's location during exercise. The system is capable of determining that the environment confounder is present or detected in response to determining that the current PM, or PM found while evaluating ventilation threshold, is different, e.g., higher, than the PM established in the baseline data.

Regarding weather, for example, the system is capable of querying an external data source, e.g., a weather service, to obtain information such as ambient temperature. If the ambient temperature for the location of the user is different from the ambient temperature where the baseline data is established, the system may consider the difference, e.g., a difference greater than a threshold amount, a confounder.

Regarding altitude, for example, the system is capable of querying an external data source based upon location to determine altitude. In another example, the system may be coupled to an altimeter so that the sensor data includes altimeter data. Oxygen saturation decreases at higher altitudes. If the altitude of the location of the user differs from the altitude where the baseline data is established, e.g., by more than a threshold amount, the difference may affect determinations relating to ventilation threshold and be considered a confounder.

Regarding hydration, the system may have access to user data specifying hydration information. As an illustrative example, the system or another device coupled to the system may execute a hydration tracking application. The user may enter data specifying hydration into the application. The system is capable of determining whether the user is sufficiently hydrated based upon a comparison of the user's hydration data to a baseline hydration level for the user. The system, for example, is capable of detecting the hydration confounder in response to determining that the user's hydration level is below the baseline hydration level during the time immediately prior to the start of exercise.

Figure 6:
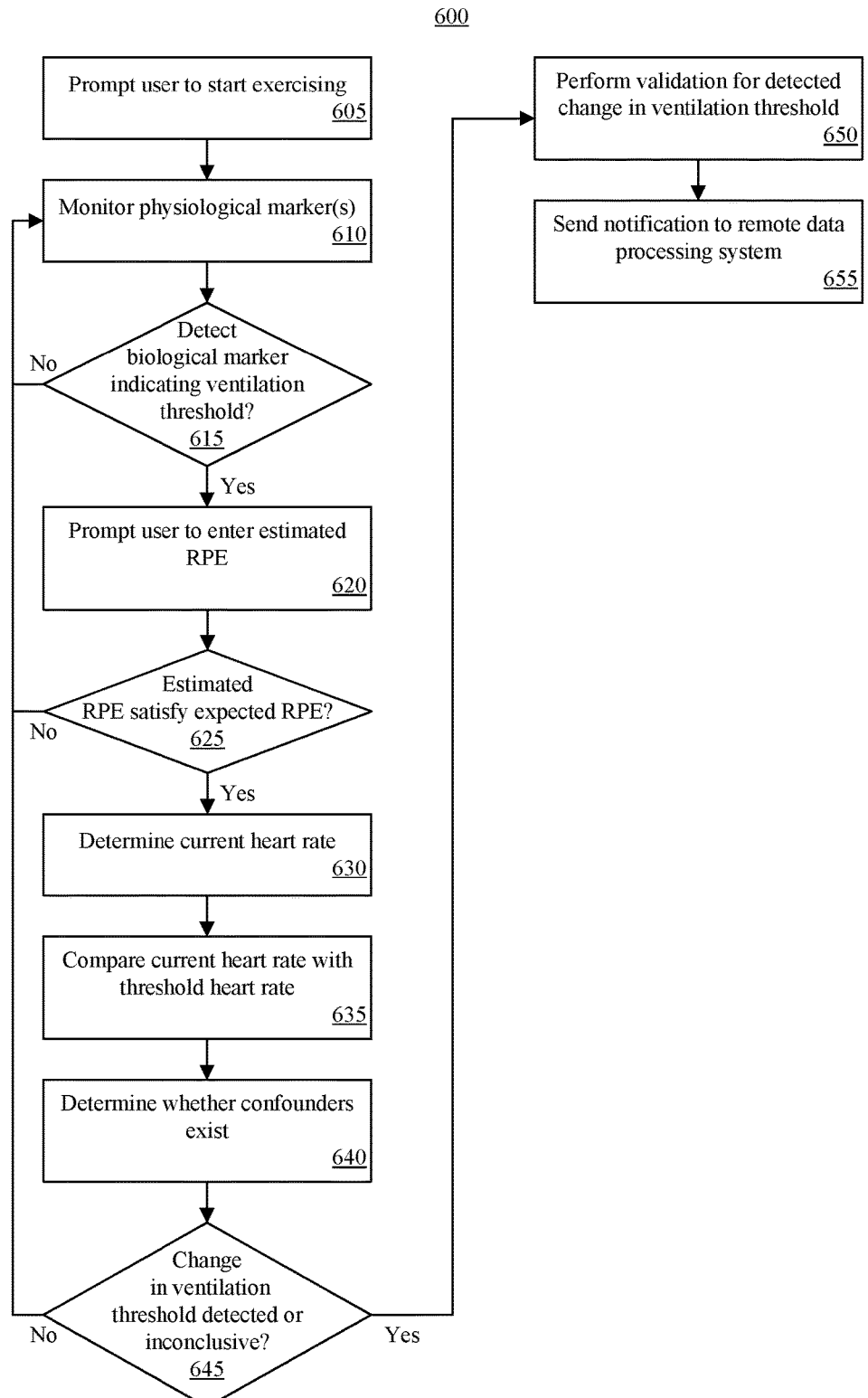
FIG. 6 illustrates another example method of evaluating ventilation threshold.

FIG. 6 illustrates another method 600 of evaluating ventilation threshold for a user. FIG. 6 illustrates a real time method of detecting ventilation threshold or a change in ventilation threshold for a user that utilizes the baseline data described in connection with FIG. 4. In an embodiment, method 600 is performed by a system as described in connection with FIG. 1.

In block 605, the system is capable of prompting the user to begin exercising. In block 610, the system is capable of monitoring for one or more biological markers. In one example, the system is capable of monitoring the respiratory sound of the user. For example, the system may store a baseline respiratory sound of the user when in ventilation threshold. The system is capable of monitoring the respiratory sound of the user using a microphone or other respiratory sensor. Thus, the system monitors the real time sensor data by comparing the real time respiratory sound of the user to the baseline respiratory sound corresponding to ventilation threshold to determine a match.

In another example, the system is capable of monitoring the total activity of the user. The system, for example, is capable of monitoring the power generated by an accelerometer over time as the user exercises. The system is capable of using the power generated by the accelerometer as a proxy or indication of total activity of the user. The system is capable of comparing the cumulative output power of the accelerometer over the time period that the user exercises with a baseline for total activity, e.g., baseline total power, previously recorded when the user reached ventilation threshold.

In block 615, the system determines whether a biological marker indicating ventilation threshold is detected. In response to detecting a biological marker, method 600 continues to block 620. If the biological marker is not detected, method 600 loops back to block 610. For example, the system is capable of determining whether the current respiratory sound of the user matches the baseline respiratory sound thereby indicating that the user has reached ventilation threshold. In another example, the system is capable of determining whether the total activity of the user matches, e.g., is equal to or greater than, the baseline total activity thereby indicating that the user has reached ventilation threshold. In still another example, the system is adapted detect both biological markers in order to continue to block 620.

In block 620, the system prompts the user to enter an estimated RPE value. For example, the system is capable of generating a user interface asking the user to enter the estimated RPE. The user interface may include a field or other user interface element through which the user may enter the estimated RPE. The system can receive a user input specifying the estimated RPE.

In block 625, the system determines whether the estimated RPE entered in block 720 satisfies an expected RPE. For example, the system is capable of determining whether the estimated RPE is greater than or equal to a threshold RPE value such as 13. An RPE value of 13, for example, is indicative that the user is at or is approaching ventilation threshold. If the estimated RPE satisfies the expected RPE (e.g., is at least 13), method 600 may continue to block 630. If the estimated RPE does not satisfy the expected RPE, e.g., the estimated RPE value is less than the threshold RPE value, method 600 may loop back to block 610 to continue monitoring as the system determines that the user has not reached ventilation threshold.

In block 630, the system is capable of determining a current heart rate for the user. The system is capable of determining the current heart rate for the user from the heart rate sensor data that is being collected. The system determines the current heart rate for the user in response to determining that ventilation threshold has been reached. In block 635, the system is capable of comparing the current heart rate with the baseline heart rate of the user for ventilation threshold.

In block 640, the system determines whether one or more confounders exist. As discussed, the system is capable of detecting physiological confounders such as activity level, homeostatic disturbances, cardiac pathology, pulmonary pathology, musculoskeletal issues, etc. The system is further capable of detecting external confounders such as environment, altitude, weather, and hydration.

In block 645, the system determines whether a change in ventilation threshold of the user has occurred. The system determines whether a change in ventilation threshold for the user has occurred based upon any detected change in heart rate from the comparison in block 635 and the existence, if any, of confounders from block 640.

If, for example, the current heart rate is lower than the baseline heart rate for ventilation threshold of the user without having detected any confounders, the system determines that a change in ventilation threshold has occurred. In particular, the system determines that the ventilation threshold of the user has decreased. If, for example, the current heart rate is higher than the baseline heart rate for ventilation threshold of the user without having detected any confounders, the system determines that a change in ventilation threshold has occurred. In particular, the system determines that ventilation threshold of the user has increased. If, for example, the system detects one or more confounders, the system determines that any change in heart rate that is detected is not determinative of whether a change in ventilation threshold for the user has occurred.

In response to determining that a change in ventilation threshold has occurred or that the result is inconclusive (e.g., due to one or more confounders), method 600 continues to block 650. In response to determining that no change in ventilation threshold has occurred, method 600 loops back to block 610 to continue processing.

In block 650, the system is capable of performing validation for a detected change in ventilation threshold. It should be appreciated that block 650 may be omitted or skipped in the case where the result is indeterminate.

In one aspect, the system is adapted to perform validation by evaluating the heart rate recovery of the user. As discussed, the system is capable of analyzing the heart rate recovery of the user to ensure that the heart rate recovery follows a bi-exponential curve. In one or more embodiments, the heart rate recovery of the user may be compared to prior heart rate recovery data, e.g., a baseline heart rate recovery for the user. The system may validate an increase in ventilation threshold by determining that the value of k in the bi-exponential expression increases when curve fitting heart rate recovery data for the user. The system may validate a decrease in ventilation threshold by determining that the value of k in the bi-exponential expression decreases when curve fitting heart rate recovery data for the user.

In block 655, the system is capable of sending a notification to a remote data processing system. The remote data processing system may be a server of a medical services provider, hospital, doctor, or the like. Examples of notifications include, but are not limited to, a text message, a short message service (SMS) message, an electronic mail, etc. The notification may state that a change in ventilation threshold for the user is detected. The notification may include additional data such as validation data, sensor data recently collected from the user, whether the ventilation threshold increased or decreased, etc.

In the case where the result is inconclusive, the system may send a notification stating that the result was inconclusive and include any additional data such as confounder(s) detected, sensor data, and the like. It should be appreciated that in one or more embodiments, the system is adapted to provide notifications specifying the foregoing types of data in cases where the system determines that ventilation threshold of the user has not changed in order to provide medical services providers with useful information relating to the user.

Figure 7:
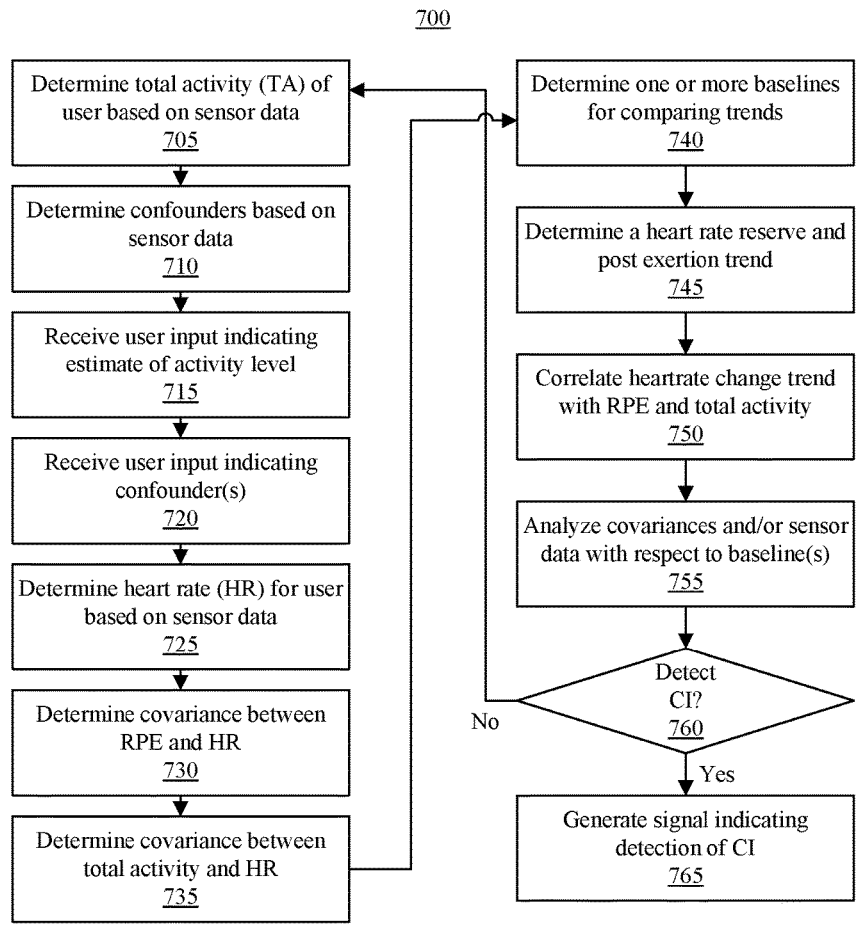
FIG. 7 illustrates an example method of detecting chronotropic incompetence.

FIG. 7 illustrates an example method 700 of detecting CI. Method 700 may be performed by a system such as the system described in connection with FIG. 1. Method 700 may begin in a state where sensor data has been collected for the patient over time, e.g., a period of time, and is available for analysis. In one or more embodiments, the system collects the sensor data. In one or more other embodiments, one or more items of sensor data or all of the sensor data may be generated from other system(s) and/or device(s) and be read and/or processed by the system performing method 700.

In block 705, the system determines the total activity or "TA" of the patient based on sensor data. The system is capable of determining the total activity for the patient using accelerometer data. In one example, the system is capable of determining the total activity for the patient based on the power of the accelerometer output.

In block 710, the system optionally determines one or more confounders relating to CI detection based on sensor data. A more detailed description of confounders in the context of CI and the automatic detection of such confounders by the system is provided herein in connection with FIG. 9.

In block 715, the system optionally receives a patient input indicating an estimate of activity level for the patient. In one or more embodiments, the estimate of the patient's activity level is a rating of perceived exertion or RPE.

In one or more other embodiments, the estimate of activity level may be determined in an automated manner by the system without querying the patient for such information. In that case, querying the patient for an estimate of activity level need not be performed. The system can be adapted to determine an estimate of activity level, e.g., an RPE, from sensor data. In one example, the system is capable of determining or estimating activity level such as RPE by detecting respiration (ventilation) related sound from the patient related to exertion from audio sensor data. The system may estimate activity level or RPE by comparing progressive changes in the respiratory related sounds of the patient from audio sensor data that are indicative of exertion.

In block 720, the system optionally receives a patient input indicating one or more confounders. The system, for example, may query the patient for a list of confounders or to select those confounders applicable to the patient from a list of confounders presented to the patient. For example, the system may query the patient about medication intake. In one example, the system queries or asks the patient whether the patient is taking any beta blocker medication or any other drug that changes chronotropic nature of the function of the heart. Such medications and/or drugs may affect the measurements described below. As such, depending upon the medication and/or drugs indicated, the threshold for determining CI may be adjusted or changed.

In block 725, the system determines a heart rate (HR) for the patient based upon the sensor data. In block 730, the system determines a covariance COV(RPE, HR) between RPE and the HR. In block 735, the system determines a covariance COV(TA, HR) between the measured TA from block 705 and the HR of block 725. For example, referring to blocks 730 and 735, the system is capable of calculating covariances between any pair of the following: an HR time series, a TA time series, and RPE.

In block 740, the system determines one or more baseline cardiac health measures for comparing trends. In one or more embodiments, baseline cardiac health measures (or baselines) may be determined with the patient at rest and/or for one or more or each of the possible RPE values. The baselines may be stored for subsequent comparison with newly collected sensor data and/or patient input. Example baselines include, but are not limited to:

- a covariance COV($RPE_{Rest}$, $HR_{Rest}$) between $RPE_{Rest}$ and $HR_{Rest}$;
- a covariance between RPE and HR during exertion which can be denoted by COV($RPE_{exertion}$, $HR_{exertion}$);
- a covariance COV($HR_{Rest}$, $TA_{Rest}$) between $HR_{Rest}$ and $TA_{Rest}$ at rest;
- a covariance COV(HRR, $HR_D$) between HRR (heart rate recovery) and $HR_D$, where subscript "D" indicates deceleration trend (post-exertion) for HR with effort level and with total activity level as measured by sensors;
- a covariance COV(EEE, RPE) between EEE (exercise energy expended), as may be measured using accelerometer activity, and RPE; and/or
- a respiration related sound recorded or observed at different RPE levels.

In one or more embodiments, a baseline cardiac health measure is determined from sensor data as described within this disclosure. For example, baseline cardiac health measures may be determined while the patient is at rest or in a known state. In one or more other embodiments, a baseline cardiac health measure is a reference state or data, e.g., predetermined or fixed data, that is specified by a physician, obtained from a standard, or the like and used for purposes of comparison as described herein.

In block 745, the system optionally determines an HRR and the HRR trend post-exertion. The system further is capable of correlating the HR change trend (e.g., the deceleration trend) with the RPE and with the measured TA of block 705. In an aspect, the system is capable of determining whether the heart rate recovery has a bi-exponential trend. For example, the system is capable of examining the logarithm of HRR for bi-exponentiality. The absence of a bi-exponential trend indicates CI. In block 750, the system optionally correlates HR change trend with RPE and total activity.

In block 755, the system is capable of analyzing one or more of the determined covariances and/or sensor data with respect to baselines. For example, the system is capable of detecting an anomaly such as a difference by more than a threshold from the baseline or an expected value. The lack of an expected covariance suggests detection of CI. In one embodiment, the system is capable of determining that an individual has CI responsive to determining that the covariance between energy expanded and RPE remains the same with the HR not being elevated. In other cases, where the covariance between EEE and RPE remains the same with EEE being low and RPE being high, the system is capable of determining that the individual has a reduced fitness level (e.g., not CI). The system is capable of calculating a cardiac health measure, including any of the covariances described herein, from sensor data to compare with a baseline cardiac health measure (e.g., a baseline covariance) to determine or estimate whether the patient has CI.

In one or more embodiments, the system is capable of adjusting the threshold for CI based upon medication intake or other confounders as determined in block 720. In one or more other embodiments, the threshold for CI is adjusted based upon one or more confounders detected within the sensor data from block 710. Examples of confounders include, but are not limited to, stress; sleep deprivation; tiredness; depression (mood); consumption of stimulants (caffeine, intoxicants etc.); any other drug that may have an effect on blood pressure and/or HR; state of health including fever, dehydration, or any other condition where HR and/or blood pressure, or other ANS markers can be reasonably expected to undergo significant change; and so forth. In one or more embodiments, the threshold for detecting CI is adjusted upward or downward based upon whether one or more of the confounders are detected within the sensor data. Confounders and the automated detection thereof from sensor data in the context of CI are discussed in further detail in connection with FIG. 9.

In one or more embodiments, the system is capable of accounting for confounders by computing the Relative Increase in HR (RIHR). RIHR is also called Increment % from HR at rest to Peak HR. RIHR may be calculated using the expression [(Peak HR−HR at Rest)/(HR at Rest)]×100.

In some cases, for individuals with CI that are taking beta blockers, a modified HR reserve may be used to account for confounders. The modified HR reserve (MHRR) may be calculated using the expression [(Increment % from HR at rest to peak HR)/(220−Age−HR at rest)]×100. Typically, HR reserve is calculated using the expression [(Peak HR−HR at rest)/(220−Age−HR at rest)]×100. The system further is capable of computing MHRR in one or more embodiments. It should be appreciated that HR reserve can also be calculated by estimating the Peak HR via any other varieties of accepted formulas that correlate expected peak HR with a person's age.

Using either RIHR or MHRR moves from an absolute calculation to a relative calculation for instances where HR may be depressed due to confounders. These relative calculations facilitate accurate detection of CI in instances where the HR increase is supposed to be larger if the HR at rest in the RIHR and/or MHRR expressions is modified to reflect or imply a baseline HR for a given instance. The system, for example, may calculate a baseline HR (e.g., the HR at rest) by measuring HR for an appropriate period of rest preceding the given exercise at a reasonably close time interval.

Using the RIHR and/or MHRR, CI detection may be performed subject to any confounders. It should be appreciated that the techniques described herein may be further modified to account for one or more confounders responsive to determining an approximation of the impact the confounder may have. For example, if the HR of an individual is typically elevated by 5 beats per minute (BPM) after caffeine consumption, then even without determining the baseline HR for a given instance, the HR may be selected from historical data. The system is capable of adding the 5 BPM, e.g., a predetermined number of beats, to the historical HR to account for the caffeine consumption.

In block 760, the system determines whether one or more indicators of CI are detected. If so, method 700 proceeds to block 765. If not, method 700 may loop back to block 705 to continue processing. In block 765, the system generates a signal or notification that is output indicating that CI is detected. In one or more embodiments, responsive to detecting CI, the system is capable of providing an indication to a remote system. For example, the system is capable of providing a message or indication to a healthcare provider server based on the computed information.

While the above description is described in the context of computing covariance, alternative embodiments can use other similarity measures or dissimilarity measures, such as correlation or distance functions. Further, one or more or each of the calculations described in connection with FIG. 7 can be contextual. For example, the CI of a patient may be different in morning vs. in evening due to the circadian rhythm of various hormones secreted by the patient's endocrine system. In this regard, the CI threshold that is used may be varied according to context such as morning vs. evening.

Figure 8:
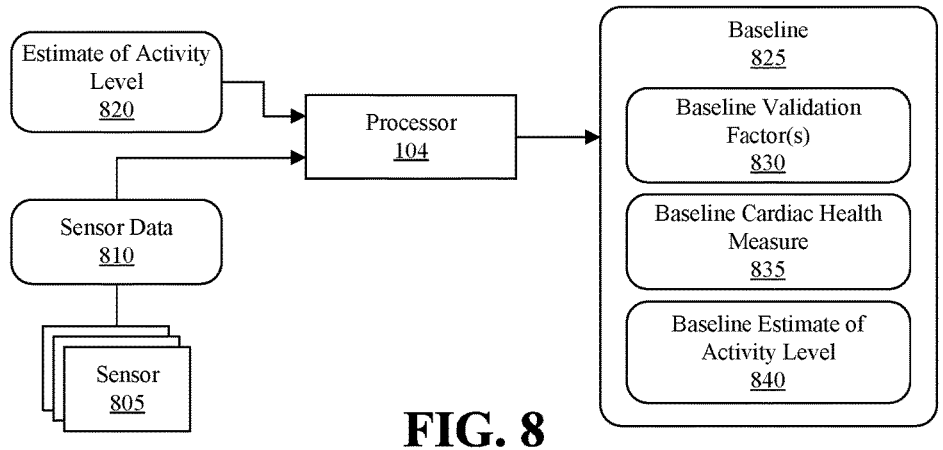
FIG. 8 illustrates an example of baseline generation for chronotropic incompetence detection.

FIG. 8 illustrates an example of baseline generation for CI detection. Baseline generation may be performed at any of a variety of different times in order to establish one or more baselines for purposes of detecting CI in a patient. In one or more embodiments, baseline generation may be performed as part of an intake or onboarding process of a rehabilitation program. For example, a patient may be asked to perform one or more tasks, activities, or exercises. During that time, baseline 825 may be generated or otherwise determined. The baselines determined may be stored in the patient's system for purposes of later comparison.

As shown, one or more sensors 805 are capable of generating sensor data 810. Example sensors 805, as discussed with reference to FIG. 1, include, but are not limited to, an accelerometer, a heart rate sensor, a microphone, and so forth. Sensor data 810 is generated over a period of time. Accordingly, for the various values and/or quantities described, it should be appreciated that sensor data 810 includes a time series of such data. Sensor data 810 may be stored in a memory (not shown). As such, processor 104 may access (read and/or write) sensor data 810.

Processor 104 is also capable of receiving an estimate of activity level (EAL) 820 for the patient. EAL 820 may be provided by way of a received patient input. As noted, a system may query a patient for EAL 820. In another aspect, EAL 820 may be entered by the patient or an administrator responsive to asking the patient. As discussed, in one or more embodiments, EAL 820 is a rating of perceived exertion or RPE.

Processor 104 is capable of operating on sensor data 810 and EAL 820 to generate a baseline 825. In the example of FIG. 8, baseline 825 includes a baseline cardiac health measure 835 and baseline EAL 840. Processor 104 is capable of determining a cardiac health measure for the patient from sensor data 810 as generated by a sensor at or about the time that EAL 820 is received. Processor 104 stores the determined cardiac health measure as baseline cardiac health measure 835 in association with EAL 820 as part of baseline 825. EAL 820, when stored as part of baseline 825, is referred to as the "baseline EAL" 840.

In one or more embodiments, the baseline cardiac health measure is HR. In one or more other embodiments, the baseline cardiac health measure is one or more of the covariances described herein. In one or more other embodiments, the baseline cardiac health measure is one or more or a combination of HR and one or more of the covariances.

In one or more embodiments, processor 104 is capable of determining one or more baseline validation factors 830 from sensor data 810 for the time period within sensor data 810 for which baseline HR 835 is determined. In the example of FIG. 8, a "validation factor" refers to one or more items of data determined from sensor data 810 other than items of sensor data used to determine baseline cardiac health measure 835, that is used to validate an EAL received from the patient. Appreciably, the time and/or time period for which a baseline validation factor 830 is determined for baseline 825 is the same time and/or time period for which baseline HR 835 and baseline EAL 840 are determined for baseline 825.

One example of a validation factor, including a baseline validation factor, is TA. TA, which indicates energy expended by the patient, can be measured by accelerometer data that is included in sensor data 810. TA may be determined as previously described herein with reference to FIG. 7, for example. Processor 104 operates on accelerometer data to measure the energy expended, e.g., an amount of work for a given time or period of time, performed by the patient. In one or more embodiments, processor 104 is configured to include or read additional attributes of the patient such as height, weight, and age (or any other relevant parameters such as extra non-physiological weight the user is carrying) in order to more accurately calculate the expended energy of the patient as a baseline validation factor 830.

Another example of a validation factor, including a baseline validation factor, is respiratory sound indicating exertion. The respiratory sound may indicate a level of exertion for a patient indicating a level of difficulty. The microphone generates audio data that is included in sensor data 810. Processor 104 operates on the audio data to measure respiratory indications for exertion for a given time or period of time, for the patient. For example, processor 104 is capable of detecting breathing sounds (e.g., breath, wheezing, coughing, etc.) within the audio data and determining the characteristics of the breathing sounds as a baseline validation factor 830. The respiratory sound may be analyzed for different RPE to determine baselines for the different RPE.

Accordingly, baseline validation factor(s) 830 may be stored with baseline cardiac health measure 835 and baseline EAL 840 within baseline 825. By storing baseline validation factor(s) 830 as part of baseline 825, when baseline 825 is later used for purposes of evaluating cardiac health of the patient, newly determined validation factors may be compared with baseline validation factors 830 for a given EAL and/or cardiac health measure. The validation process is described in greater detail with reference to FIG. 9.

In the example of FIG. 8, while one baseline is illustrated, it should be appreciated that the operations described may be performed one or more additional times in order to generate further baselines. In one example, a baseline may be generated for one or more or for each possible value of the estimate of activity level or RPE. Referring to Table 1, for example, a baseline may be generated for each possible score for the RPE from 6 to 20.

Figure 9:
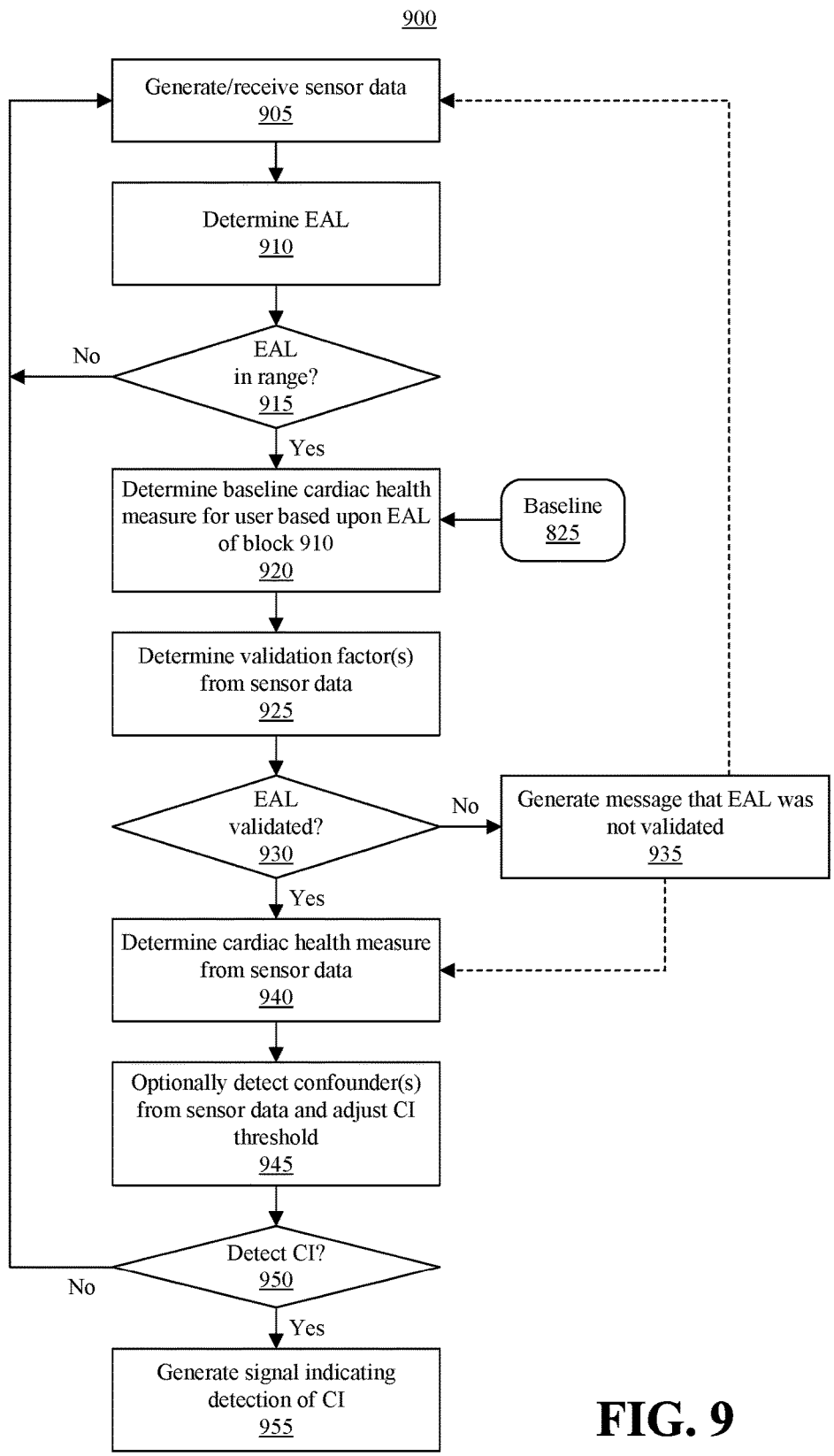
FIG. 9 illustrates another example method of detecting chronotropic incompetence.

FIG. 9 illustrates another example method 900 of detecting CI. Method 900 may be performed by a system as described in connection with FIG. 1. Method 600 may begin in a state where one or more baselines as described herein with reference to FIGS. 7 and 8 are generated and stored. The baselines are available for use by the system in detecting CI.

In block 905, the system generates or receives sensor data. As noted, in one or more embodiments, the system collects the sensor data. In one or more other embodiments, one or more items of sensor data or all of the sensor data may be generated from other system(s) and/or device(s) and be read or received by the system performing method 900. In block 910, the system determines an EAL. In one or more embodiments, the system queries the patient for an EAL. The system receives a patient input specifying the EAL. In one or more other embodiments, the system is capable of estimating an EAL based upon respiratory sounds as previously described.

In block 915, the system determines whether the EAL is in a defined range. If so, method 900 continues to block 920. If not, method 900 loops back to block 905 to continue processing. In one or more embodiments, the EAL must be within a particular range in order to detect CI. In one example, the range is an RPE of 13 or 14. In that case, if the EAL specifies an RPE of 13 or 14, method 900 continues to block 920. If not, method 900 loops back to block 905 to continue processing.

In block 920, the system determines the baseline cardiac health measure for the patient based upon the EAL determined in block 910. For example, the system uses the EAL determined in block 910 and locates a matching baseline EAL within the baselines. As discussed with reference to FIG. 8, for example, each baseline stores a baseline EAL. If, for example, the EAL of block 910 is an RPE value of 13, the system looks up the baseline having a baseline EAL with an RPE value of 13. If, for example, the EAL of block 910 is an RPE value of 14, the system looks up the baseline having a baseline EAL with an RPE value of 14. For purposes of discussion, the system is capable of looking up baseline 825 using the EAL determined in block 910 as the baseline EAL and determining the baseline cardiac health measure from baseline 825. As noted, in one or more embodiments, the baseline cardiac health measure is HR, but may be or include one or more of the covariances described.

In block 925, the system is capable of determining one or more validation factors from the sensor data. The validation factors may be determined for the same time and/or same period of time to which the EAL determined in block 910 corresponds. For example, the system is capable of determining the validation factor of activity level from accelerometer sensor data and/or characteristics of respiratory sound indicating exertion from audio sensor data.

In block 930, the system is capable of validating the EAL received in block 910. In one or more embodiments, the system validates the EAL of block 910 by comparing one or more of the validation factors determined in block 925 with the corresponding baseline validation factor(s), e.g., validation factor(s) of the same type, from the baseline used to determine the baseline cardiac health measure. For example, the system may compare one or more of the validation factors determined in block 925 using current sensor data with the stored baseline validation factor(s) 830 of baseline 825.

As an illustrative example, the system may validate the EAL of block 910 by determining that the characteristics of respiratory sound indicating exertion determined in block 925 are within a predetermined threshold of, or match, baseline characteristics of respiratory sound indicating exertion specified in baseline validation factor(s) 830. As another illustrative example, the system may validate the EAL of block 910 by determining that the TA determined in block 925 is within a predetermined threshold or amount of a baseline TA specified in baseline validation factor(s) 830.

In still another illustrative example, the system may validate the EAL of block 910 by determining that the characteristics of respiratory sound determined in block 925 is/are the same as or similar to the characteristics of respiratory sound specified in baseline validation factor(s) 830 and that the total activity determined in block 925 is within a predetermined threshold or amount of a baseline total activity specified in baseline validation factor(s) 830.

In one or more embodiments, where the EAL is determined automatically from respiratory sound, the system may utilize a validation factor other than respiratory sound to perform validation.

Block 930 ensures that the EAL provided by the patient is consistent. In the event that the patient begins to provide inconsistent EALs, one or more of the validation factors will likely mismatch the baseline validation factors. For example, in the case where the patient over estimates the EAL, the validation factors will likely be lower than the baseline validation factors obtained from baseline 825, e.g., lower than the predetermined threshold or amount.

In any case, if the EAL is validated, method 900 may continue to block 940. If the EAL is not validated, method 900 may proceed to block 935. In block 935, the system may generate a message or notification that the EAL was not validated or that validation was not successful. In one or more embodiments, after block 935, method 900 may loop back to block 905 to continue processing. In one or more other embodiments, after block 935, method 900 may continue to block 940. For example, method 900 may continue to block 940 to detect CI despite the unsuccessful validation of the EAL. In that case, where CI is detected, the signal indicating detection of CI in block 955 may further indicate that while CI is detected, validation of the EAL was unsuccessful.

In block 940, the system is capable of determining a cardiac health measure for the patient from the sensor data. In one embodiment, the cardiac health measure is HR. The system is capable of determining the HR for the patient from the sensor data for the same time or same time period as the EAL received in block 920. In one or more other embodiments, the cardiac health measure is one or more covariances and/or a combination of HR and one or more covariances.

In block 945, the system optionally detects one or more confounders from the sensor data and adjusts a CI threshold. In one or more embodiments, the system is capable of detecting one or more confounders from the sensor data. Responsive to detecting a confounder in the sensor data, the system adjusts the CI threshold. In one or more embodiments, the CI threshold specifies how far the patient's HR, as determined in block 940, must be from a baseline HR (e.g., the baseline cardiac health measure) of block 920 for the system to detect CI. The CI threshold may be expressed as a percentage, a predetermined amount, or the like.

In one example, the system is capable of detecting, from the sensor data, the confounder of sleep deprivation as previously described herein. In another example, the system is capable of detecting, from the sensor data, the confounder of stress as described herein in connection with homeostatic disturbances.

Responsive to detecting one or more of the confounding factors, the system adjusts the CI threshold. For example, the system increases the CI threshold. In one or more embodiments, the system increases the CI threshold a predetermined amount or percentage for each confounder detected. The system is further capable of increasing the CI threshold based upon the amount of one or more or each of the confounders detected. In one or more other embodiments, the system increases the CI threshold only responsive to determining that the, or each, confounder, while detected for the time or time period corresponding to the EAL received in block 910, was not present for the determination of the baseline HR.

In one or more other embodiments, the system is capable of using recent exertion history of the patient into account. As an illustrative example, if the patient has endured significant exertion in comparison to the patient's baseline level of exertion in a preceding time period that is sufficiently close to the time period being evaluated for CI, the patient is likely tired. As such, the patient is likely to indicate a high RPE despite the effort level for that given instance or period of time not really being high. Thus, in one or more embodiments, the system is capable of excluding instances of higher than baseline level of exertion that occur within a threshold or predetermined amount of time of an earlier period or instance of higher than baseline level of exertion from consideration in CI detection.

In block 950, the system determines whether CI is detected for the patient. In one or more embodiments, the system compares the HR determined in block 940 with the baseline HR determined in block 920. The system is capable of determining whether the HR is within the CI threshold of the baseline HR. In one example, the CI threshold is 80% of the baseline HR. If the HR is within the threshold or predetermined amount of the baseline HR, the system does not detect CI for the patient. Accordingly, method 900 may loop back to block 905. If the HR is not within the threshold or predetermined amount of the baseline HR, the system detects CI for the patient. In that case, method 900 continues to block 955.

In some cases, the system is configured to adjust the CI threshold. In one or more embodiments, the system is capable of measuring the fraction of HR reserve achieved after exercise. In that case, where the patient is starting with a higher HR than the patient's HR at rest, rather than using HR at rest, the system may compute the fraction of HR increase achieved by using the HR (during an inactive period) immediately prior to the period of exercise.

In other cases, the HR increase experienced by a patient may be affected by stress, a medical condition, and/or a medication. These effects may be determined by using a circadian baseline of the patient that is annotated with events and times. The circadian baseline, for example, may indicate events such as ingestion of caffeine and/or medication and times. Stress may be detected automatically. In one or more embodiments, the system is capable of receiving data indicating stress, medical condition, and/or medication from a medical provider and/or medical provider system.

In block 955, the system generates a signal or notification that is output indicating that CI is detected. In one or more embodiments, responsive to detecting CI, the system is capable of providing an indication to a remote system. For example, the system is capable of providing a message or indication to a healthcare provider server based on the computed information.

Referring to FIGS. 7 and 9, based upon the above calculations such as the presence and/or lack of covariance and/or the comparisons described, the system is capable of not only detecting CI, but also of detecting or determining improvement in CI. Improvement in CI can be a significant marker of improved health, and reduced mortality and morbidity. Conversely, worsening CI can imply a greater risk of mortality and morbidity and thus requires additional and appropriate clinical attention from the caretaking staff.

In one or more other embodiments, additional sensors may be incorporated to provide measurements that, if available, may be used as validation factors and/or to detect confounders. For example, electroencephalogram (EEG) and/or ECG data may be used to detect confounders. Visual images and/or video as may be obtained from a camera sensor may be used to aid in detecting sleep deprivation.

The terminology used herein is for the purpose of describing particular embodiments only and is not intended to be limiting. Notwithstanding, several definitions that apply throughout this document now will be presented.

As defined herein, the singular forms "a," "an," and "the" are intended to include the plural forms as well, unless the context clearly indicates otherwise. As defined herein, the terms "at least one," "one or more," and "and/or," are open-ended expressions that are both conjunctive and disjunctive in operation unless explicitly stated otherwise. For example, each of the expressions "at least one of A, B, and C," "at least one of A, B, or C," "one or more of A, B, and C," "one or more of A, B, or C," and "A, B, and/or C" means A alone, B alone, C alone, A and B together, A and C together, B and C together, or A, B and C together. As defined herein, the term "automatically" means without user intervention.

As defined herein, the term "computer readable storage medium" means a storage medium that contains or stores program code for use by or in connection with an instruction execution system, apparatus, or device. As defined herein, a "computer readable storage medium" is not a transitory, propagating signal per se. A computer readable storage medium may be, but is not limited to, an electronic storage device, a magnetic storage device, an optical storage device, an electromagnetic storage device, a semiconductor storage device, or any suitable combination of the foregoing. Memory elements, as described herein, are examples of a computer readable storage medium. A non-exhaustive list of more specific examples of a computer readable storage medium may include: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, or the like.

As defined herein, the term "if" means "when" or "upon" or "in response to" or "responsive to," depending upon the context. Thus, the phrase "if it is determined" or "if [a stated condition or event] is detected" may be construed to mean "upon determining" or "in response to determining" or "upon detecting [the stated condition or event]" or "in response to detecting [the stated condition or event]" or "responsive to detecting [the stated condition or event]" depending on the context.

As defined herein, the terms "one embodiment," "an embodiment," or similar language mean that a particular feature, structure, or characteristic described in connection with the embodiment is included in at least one embodiment described within this disclosure. Thus, appearances of the phrases "in one embodiment," "in an embodiment," and similar language throughout this disclosure may, but do not necessarily, all refer to the same embodiment. The terms "embodiment" and "arrangement" are used interchangeably within this disclosure.

As defined herein, the term "processor" means at least one hardware circuit configured to carry out instructions contained in program code. The hardware circuit may be an integrated circuit. Examples of a processor include, but are not limited to, a central processing unit (CPU), an array processor, a vector processor, a digital signal processor (DSP), a field-programmable gate array (FPGA), a programmable logic array (PLA), an application specific integrated circuit (ASIC), programmable logic circuitry, and a controller.

As defined herein, the term "real time" means a level of processing responsiveness that a user or system senses as sufficiently immediate for a particular process or determination to be made, or that enables the processor to keep up with some external process.

As defined herein, the term "user" means a human being.

The terms first, second, etc. may be used herein to describe various elements. These elements should not be limited by these terms, as these terms are only used to distinguish one element from another unless stated otherwise or the context clearly indicates otherwise.

A computer program product may include a computer readable storage medium (or media) having computer readable program instructions thereon for causing a processor to carry out aspects of the present invention. Within this disclosure, the term "program code" is used interchangeably with the term "computer readable program instructions." Computer readable program instructions described herein may be downloaded to respective computing/processing devices from a computer readable storage medium or to an external computer or external storage device via a network, for example, the Internet, a LAN, a WAN and/or a wireless network. The network may include copper transmission cables, optical transmission fibers, wireless transmission, routers, firewalls, switches, gateway computers and/or edge devices including edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations for the inventive arrangements described herein may be assembler instructions, instruction-set-architecture (ISA) instructions, machine instructions, machine dependent instructions, microcode, firmware instructions, or either source code or object code written in any combination of one or more programming languages, including an object oriented programming language and/or procedural programming languages. Computer readable program instructions may specify state-setting data. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a LAN or a WAN, or the connection may be made to an external computer (for example, through the Internet using an Internet Service Provider). In some cases, electronic circuitry including, for example, programmable logic circuitry, an FPGA, or a PLA may execute the computer readable program instructions by utilizing state information of the computer readable program instructions to personalize the electronic circuitry, in order to perform aspects of the inventive arrangements described herein.

Certain aspects of the inventive arrangements are described herein with reference to flowchart illustrations and/or block diagrams of methods, apparatus (systems), and computer program products. It will be understood that each block of the flowchart illustrations and/or block diagrams, and combinations of blocks in the flowchart illustrations and/or block diagrams, may be implemented by computer readable program instructions, e.g., program code.

These computer readable program instructions may be provided to a processor of a computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. In this way, operatively coupling the processor to program code instructions transforms the machine of the processor into a special-purpose machine for carrying out the instructions of the program code. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the operations specified in the flowchart and/or block diagram block or blocks.

The computer readable program instructions may also be loaded onto a computer, other programmable data processing apparatus, or other device to cause a series of operations to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various aspects of the inventive arrangements. In this regard, each block in the flowchart or block diagrams may represent a module, segment, or portion of instructions, which comprises one or more executable instructions for implementing the specified operations. In some alternative implementations, the operations noted in the blocks may occur out of the order noted in the figures. For example, two blocks shown in succession may be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, may be implemented by special purpose hardware-based systems that perform the specified functions or acts or carry out combinations of special purpose hardware and computer instructions.

One or more embodiments are directed to systems and/or apparatus for evaluating ventilation threshold. In one aspect, an apparatus includes a sensor adapted to generate sensor data, a memory adapted to store a baseline RPE, a baseline heart rate, and a biological marker, each corresponding to ventilation threshold for a user, and a processor coupled to the memory and the sensor. The processor is adapted to receive an input specifying an estimate of RPE in response to determining that the sensor data matches the biological marker, determine a current heart for the user from the sensor data in response to determining that the baseline RPE is achieved based upon the input, and compare the current heart rate for the user with the baseline heart rate to detect a change in ventilation threshold for the user. The processor is further adapted to send a notification in response to detecting the change in the ventilation threshold for the user.

In an aspect, the current sensor data is real time sensor data.

In another aspect, the change in ventilation threshold is a reduction in ventilation threshold detected in response to determining that the current heart rate for the user is lower than the baseline heart rate.

In another aspect, the biological marker includes respiratory sound for the user at the threshold RPE.

In another aspect, the biological marker includes activity level of the user at the threshold RPE.

In another aspect, the processor is further adapted to validate the detected change in ventilation threshold for the user based upon heart rate recovery.

In another aspect, the processor is further adapted to analyze the sensor data to detect a confounder, wherein the reduction in ventilation threshold is only detected for the user in response to determining that the sensor data is free of confounders.

In another aspect, the confounder includes at least one of a physiological confounder or an external confounder.

One or more embodiments are directed to methods of evaluating ventilation threshold. In one aspect, a method includes determining, using a processor, a baseline RPE, a baseline heart rate, and a biological marker each corresponding to ventilation threshold for a user, receiving, using the processor, an input specifying an estimate of RPE in response to determining that sensor data matches the biological marker, and determining, using the processor, a current heart rate for the user from the sensor data in response to determining that the baseline RPE is achieved based upon the input. The method further includes comparing, using the processor, the current heart rate for the user with the baseline heart rate to detect a change in ventilation threshold for the user and sending a notification in response to detecting the change in the ventilation threshold for the user.

In an aspect, the current sensor data is real time sensor data.

In another aspect, the change in ventilation threshold is a reduction in ventilation threshold detected in response to determining that the current heart rate for the user is lower than the baseline heart rate.

In another aspect, the biological marker includes respiratory sound for the user at the threshold RPE.

In another aspect, the biological marker includes activity level of the user at the threshold RPE.

In another aspect, the method includes validating the detected change in ventilation threshold for the user based upon heart rate recovery.

In another aspect, the method includes analyzing the sensor data to detect a confounder, wherein the reduction in ventilation threshold is only detected for the user in response to determining that the sensor data is free of confounders.

In another aspect, the confounder includes at least one of a physiological confounder or an external confounder.

One or more embodiments are directed to computer program products for evaluating ventilation threshold. In one aspect, a computer program product includes a computer readable storage medium having program code stored thereon. The program code is executable by a processor to perform executable operations. The executable operations include determining a baseline RPE, a baseline heart rate, and a biological marker each corresponding to ventilation threshold for a user, receiving an input specifying an estimate of RPE in response to determining that sensor data matches the biological marker, and determining a current heart rate for the user from the sensor data in response to determining that the baseline RPE is achieved based upon the input. The executable operations further can include comparing the current heart rate for the user with the baseline heart rate to detect a change in ventilation threshold for the user and sending a notification in response to detecting the change in the ventilation threshold for the user.

In an aspect, the current sensor data is real time sensor data.

In another aspect, the change in ventilation threshold is a reduction in ventilation threshold detected in response to determining that the current heart rate for the user is lower than the baseline heart rate.

In another aspect, the biological marker includes respiratory sound for the user at the threshold RPE.

In another aspect, the biological marker includes activity level of the user at the threshold RPE.

In another aspect, the executable operations include validating the detected change in ventilation threshold for the user based upon heart rate recovery.

In another aspect, the executable operations include analyzing the sensor data to detect a confounder, wherein the reduction in ventilation threshold is only detected for the user in response to determining that the sensor data is free of confounders.

In another aspect, the confounder includes at least one of a physiological confounder or an external confounder.

The corresponding structures, materials, acts, and equivalents of all means or step plus function elements that may be found in the claims below are intended to include any structure, material, or act for performing the function in combination with other claimed elements as specifically claimed.

The description of the embodiments provided herein is for purposes of illustration and is not intended to be exhaustive or limited to the form and examples disclosed. The terminology used herein was chosen to explain the principles of the inventive arrangements, the practical application or technical improvement over technologies found in the marketplace, and/or to enable others of ordinary skill in the art to understand the embodiments disclosed herein. Modifications and variations may be apparent to those of ordinary skill in the art without departing from the scope and spirit of the described inventive arrangements. Accordingly, reference should be made to the following claims, rather than to the foregoing disclosure, as indicating the scope of such features and implementations.

What is claimed is:

1. An apparatus for monitoring health status of a user, comprising:
   a photoplethysmography sensor adapted to generate photoplethysmography sensor data;

a memory adapted to store a baseline biological marker for the user, wherein the baseline biological marker includes respiratory rhythm, heart rate, and a rating of perceived exertion corresponding to an occurrence of ventilation threshold;

a processor coupled to the memory and the sensor, wherein the processor is adapted to:
  in response to receiving a user input specifying that a maximum rating of perceived exertion for the user is reached indicating a subsequent occurrence of ventilation threshold, determine a biological marker from the photoplethysmography sensor data, wherein the biological marker includes respiratory rhythm and heart rate corresponding to the subsequent occurrence of ventilation threshold;
  compare the biological marker determined from the photoplethysmography sensor data with the baseline biological marker stored in the memory; and
  in response to detecting a difference between the biological marker and the baseline biological marker, provide a notification indicating a change in health status.

2. The apparatus of claim 1, wherein the difference indicates a deterioration in the biological marker compared to the baseline biological marker and the notification is to reduce physical activity.

3. The apparatus of claim 1, wherein the baseline biological marker includes activity level of the user.

4. A method of monitoring health status of a user, comprising:
  storing a baseline biological marker for the user, wherein the baseline biological marker includes respiratory rhythm, heart rate, and a rating of perceived exertion corresponding to an occurrence of ventilation threshold;
  receiving, using the processor, photoplethysmography sensor data;
  in response to receiving a user input specifying that a maximum rating of perceived exertion for the user is reached indicating a subsequent occurrence of ventilation threshold, determining, using the processor, a biological marker from the photoplethysmography sensor data, wherein the biological marker includes respiratory rhythm and heart rate corresponding to the subsequent occurrence of ventilation threshold;
  comparing, using the processor, the biological marker determined from the photoplethysmography sensor data with the baseline biological marker; and
  in response to detecting a difference between the biological marker and the baseline biological marker, providing, using the processor, a notification indicating a change in health status.

5. The method of claim 4, wherein the difference indicates a deterioration in the biological marker compared to the baseline biological marker and the notification is to reduce physical activity.

6. The method of claim 4, wherein the baseline biological marker includes activity level of the user.

7. A computer program product comprising a non-transitory computer readable storage medium having program code stored thereon for monitoring health status of a user, the program code executable by a processor to perform operations comprising:
  storing a baseline biological marker for the user, wherein the baseline biological marker includes respiratory rhythm, heart rate, and a rating of perceived exertion corresponding to an occurrence of ventilation threshold;
  receiving photoplethysmography sensor data;
  in response to receiving a user input specifying that a maximum rating of perceived exertion for the user is reached indicating a subsequent occurrence of ventilation threshold, determining a biological marker from the photoplethysmography sensor data, wherein the biological marker includes respiratory rhythm and heart rate corresponding to the subsequent occurrence of ventilation threshold;
  comparing the biological marker determined from the photoplethysmography sensor data with the baseline biological marker; and
  in response to detecting a difference between the biological marker and the baseline biological marker, providing a notification indicating a change in health status.

8. The computer program product of claim 7, wherein the difference indicates a deterioration in the biological marker compared to the baseline biological marker and the notification is to reduce physical activity.

9. The computer program product of claim 7, wherein the baseline biological marker includes activity level of the user.

10. An apparatus for evaluating ventilation threshold, comprising:
  a photoplethysmography sensor adapted to generate photoplethysmography sensor data;
  a memory adapted to store a baseline rating of perceived exertion (RPE), a baseline heart rate, and a biological marker each corresponding to ventilation threshold for a user,
  a processor coupled to the memory and the photoplethysmography sensor, wherein the processor is adapted to:
  receive an input specifying an estimate of RPE in response to determining that the photoplethysmography sensor data matches the biological marker:
  determine a current heart rate for the user from the photoplethysmography sensor data in response to determining that the baseline RPE is achieved based upon the input;
  compare the current heart rate for the user with the baseline heart rate to detect a change in ventilation threshold for the user; and
  send a notification in response to detecting the change in the ventilation threshold for the user.

* * * * *